United States Patent [19]
Garrone et al.

[11] Patent Number: 5,959,085
[45] Date of Patent: Sep. 28, 1999

[54] HUMAN MONOCLONAL ANTIBODIES AGAINST HUMAN CYTOKINES AND METHODS OF MAKING AND USING SUCH ANTIBODIES

[75] Inventors: Pierre Garrone, Lyons; Odile Djossou, Francheville; Francois Fossiez, Craponne; Jacques Banchereau, Ecully, all of France

[73] Assignee: Schering Corporation, Kenilworth, N.J.

[21] Appl. No.: 08/646,367

[22] PCT Filed: Nov. 21, 1994

[86] PCT No.: PCT/US94/13188

§ 371 Date: May 16, 1996

§ 102(e) Date: May 16, 1996

[87] PCT Pub. No.: WO95/14780

PCT Pub. Date: Jun. 1, 1995

[30] Foreign Application Priority Data

Nov. 23, 1993 [EP] European Pat. Off. .............. 93402846

[51] Int. Cl.⁶ .......................... C07K 16/00; C07H 21/04
[52] U.S. Cl. .................................. 530/387.3; 530/388.1; 530/388.15; 530/388.23; 530/387.1; 536/23.53; 435/240.27; 435/252.3
[58] Field of Search ................ 530/387.1, 388.1, 530/388.15, 388.23; 536/23.53; 435/240.27, 252.3

[56] References Cited

U.S. PATENT DOCUMENTS 4,946,778  8/1990  Ladner et al. ........................ 435/69.6

FOREIGN PATENT DOCUMENTS

| A 0 267 611 | 5/1988 | European Pat. Off. . |
|---|---|---|
| A 0 314 402 | 5/1989 | European Pat. Off. . |
| A 0 364 778 | 4/1990 | European Pat. Off. . |
| 0434879 | 3/1991 | European Pat. Off. . |
| A 0 434 879 | 7/1991 | European Pat. Off. . |
| WO 90/06371 | 6/1990 | WIPO . |
| WO 91/09115 | 7/1991 | WIPO . |

OTHER PUBLICATIONS

Roitt, I.M. (ed.) Essential Immunology, 1991. (pp. 141–142).

Svenson, M et al. 1992. Cytokine 4:125–133.

Pascual. V. et al. 1990. J. Clin. Invest. 86:1320–1328.

Goding, J.W (ed.) 1986. Monoclonal Antibodies: Principles & Practice.

*Primary Examiner*—Lila Feisee
*Assistant Examiner*—Minh-Tam Davis
*Attorney, Agent, or Firm*—Cynthia L. Foulke

[57] ABSTRACT

Human monoclonal antibodies against a human cytokine (such as a human interleukin, e.g., human IL-1α) and fragments of such antibodies are disclosed. Also disclosed are pharmaceutical compositions and methods employing the human monoclonal antibodies and fragments, methods for screening for human monoclonal antibodies against a human protein, methods for producing a cDNA library enriched in DNA encoding $V_H$ and/or $V_L$ chains of a human monoclonal antibody, cell lines for making the human monoclonal antibodies, and isolated DNA for making the human monoclonal antibodies and fragments of the invention.

8 Claims, 9 Drawing Sheets

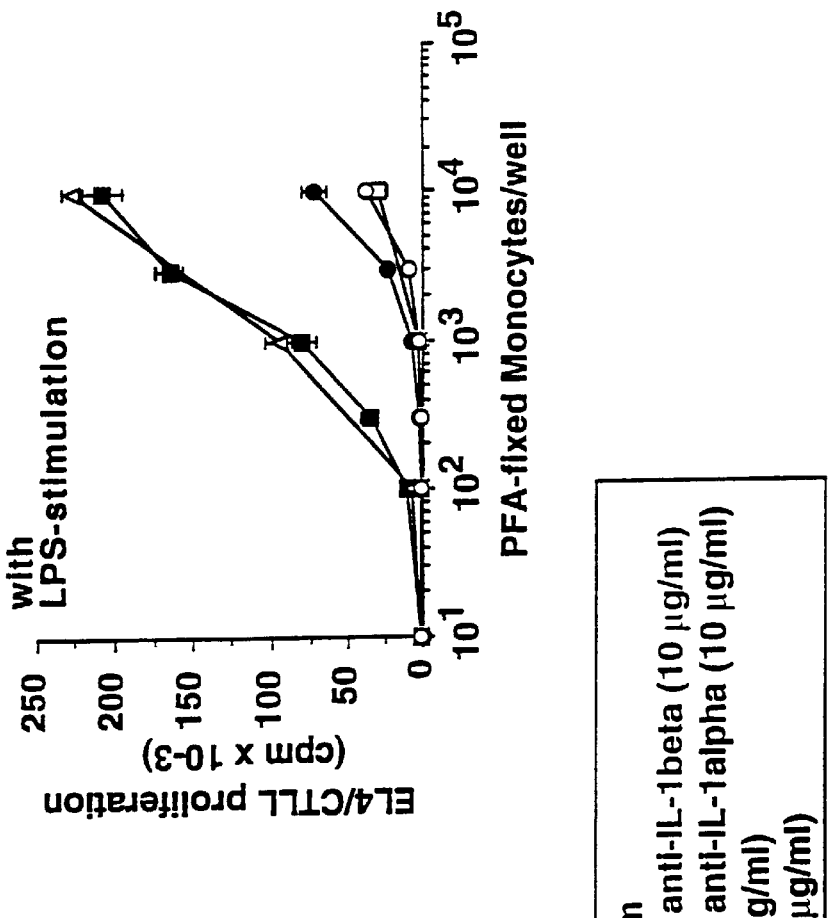
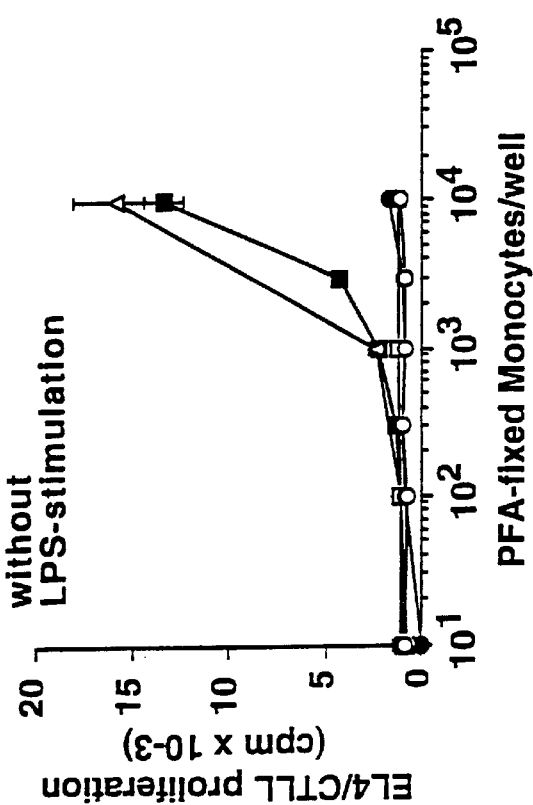
FIGURE 6A
FIGURE 6B

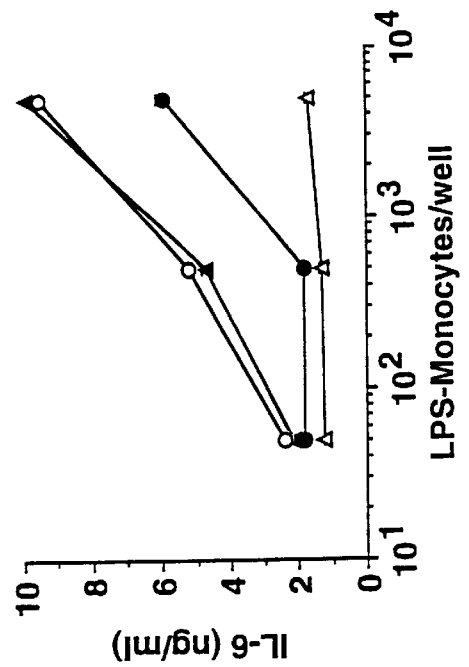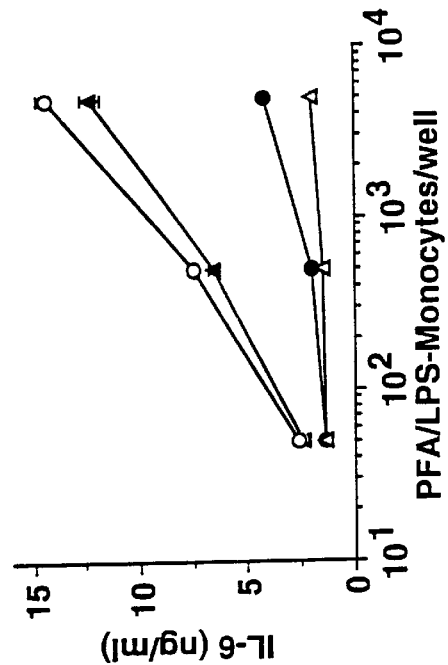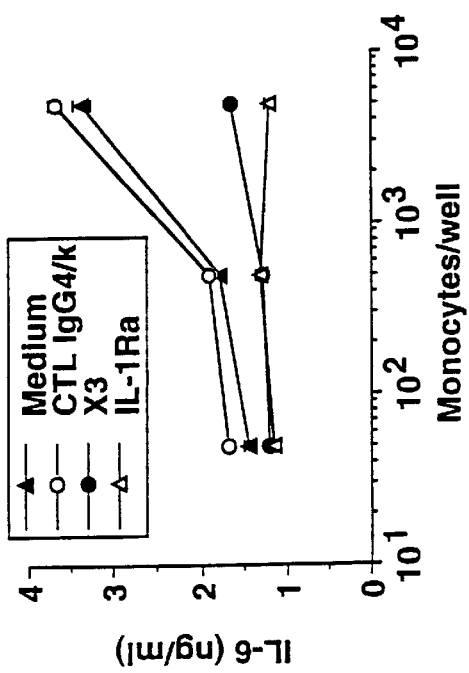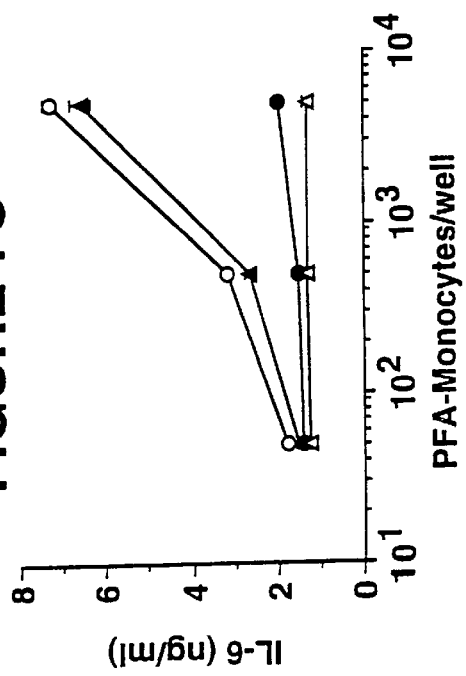

HUMAN MONOCLONAL ANTIBODIES AGAINST HUMAN CYTOKINES AND METHODS OF MAKING AND USING SUCH ANTIBODIES

The present application is the United States national application corresponding to International Application No. PCT/US94/13188, filed Nov. 21, 1994 and designating the United States, which PCT application is in turn a continuation-in-part application Ser. No. 93402846.5, filed Nov. 23, 1993, the benefit of which applications are claimed pursuant to the provisions of 35 U.S.C. 120, 363 and 365 (C).

FIELD OF THE INVENTION

The present invention relates to human monoclonal antibodies against human cytokines and methods of making, identifying and using such antibodies, preferably human monoclonal antibodies against human cytokines or lymphokines such as IL-1α, IL-1β, IL-4, IL-5, IL-6, IL-8, IL-10, TNF-α, etc.

BACKGROUND OF THE INVENTION

The applicability of human monoclonal antibodies (HuMAbs), especially HuMAbs to human cytokines, in therapy holds great promise; see, for example, Griffiths et al., *EMBO J.*, 12:725–734 (1993) and the review in Larrick et al., *J. Biol. Response Modif.*, 5:379 (1986). However, the production of useful HuMAbs against human cytokines has proved difficult.

Specifically, while the possible existence in human serum of autoantibodies to human cytokines is mentioned in numerous articles [Suzuki et al., *J. Immunol.*, 145:2140–2146 (1990) (IL-1α); Hansen et al., *Immunol. Letters*, 30:133–140 (1991) (IL-1α); Bendtzen et al., *Immunol. Today*, 11:167–169 (1990) (IL-1α and TNF-α); Bendtzen et al., *Immunol. Today*, 10:222 (1989) (IL-1α and TNF-α); Saurat et al., *J. Allergy Clin. Immunol.*, 88:244–256 (1991) (IL-1α); Suzuki et al., *Clin. Exp. Immunol.*, 85:407–412 (1991) (IL-1α); Sunder-Plassmann et al., *Kidney International*, 40:787–791 (1991) (IL-1α); Gallay et al., *Eur. Cytokine Netw.*, 2:329–338 (1991) (IL-1α and IL-1β); Mae et al., *Lymphokine Cytokine Res.*, 10:61–68 (1991) (IL-1α); Fomsgaard et al., *Scand. J. Immunol.*, 30:219 (1989) (TNF-α); Hansen et al., *Scand. J. Immunol.*, 33: 777–781 (1991) (IL-6); Crabtree et al., *Scand. J. Immunol.*, 37:65–70 (1993) (IL-8); Bost et al., *Immunology*, 65:611–615 (1988) (IL-2); Ross et al., *Clin. Exp. Immunol.*, 82:57–62 (1990) (IFN-α2b and IFN-γ); and Caruso et al., *J. Immunol.*, 144:685–690 (1990) (IFN-γ)], no one has been able to produce an isolated and purified HuMAb to a human cytokine, especially a HuMAb having high affinity, e.g., a $K_a$ of above about $10^9 M^{-1}$. Some of the reasons are pointed out in the cited article by Griffiths et al. in *EMBO. J.*:

"Human monoclonal antibodies (mAbs) have huge potential for therapy, but are difficult to make by immortalizing B-lymphocytes. Furthermore, it is especially difficult to generate human mAbs directed against human antigens (anti-self antibodies), for example antibodies against soluble TNF to block septic shock, against membrane-bound carcinoembryonic antigen to image colorectal carcinoma, or against lymphocyte antigens to destroy tumour in lymphoma. This difficulty results from immunological tolerance mechanisms that prevent the antigen-driven expansion of B-cell clones with self specificities. After antibody gene rearrangement, virgin B-cells may display antibodies with self-reactivity, but tolerance mechanisms can lead to their deletion or to their anergy. It has been suggested that cells may be anergized if the antigen is soluble, but deleted if the antigen is membrane bound. B-cell tolerance does not seem to occur when concentrations of soluble antigen are low (in contrast to T-cell tolerance) and B-cells with poor affinities for antigen are not tolerized, even at higher antigen concentrations. Such non-tolerized B-cells are not usually expanded because they lack T-cell help, although proliferation can be induced artificially by using polyclonal B-cell activators.

It is estimated that 10–30% of B-lymphocytes in normal, healthy individuals are engaged in making autoantibodies. However, the 'natural autoantibodies' produced do not lend themselves to therapeutic use as they are often IgM, low affinity and polyreactive." (Citations omitted.)

Although the Griffiths et al. article speaks of "human self-antibodies with high specificity," only single-chain $V_H$ and $V_L$ fragments are actually disclosed. Moreover, there is no disclosure in the article that any of the heavy/light-chain combinations mentioned therein are actually from one human antibody. Moreover, the human antibody fragments disclosed all have relatively low affinities, i.e., $K_a$s below $2 \times 10^7 M^{-1}$ and most below $10^7 M^{-1}$.

SUMMARY OF THE INVENTION

The present invention is directed to human monoclonal antibodies against a human cytokine and to fragments of such antibodies having an affinity for the cytokine of $10^8 M^{-1}$ or greater. The human monoclonal antibody (sometimes referred to herein as a HuMAb) or fragment preferably binds to a human lymphokine, more preferably to a human interleukin, e.g., human IL-1α, IL-1β, IL-4, IL-5, IL-6, IL-8, IL-10, IL-11, IL-12, IL-13, especially IL-1α. The human monoclonal antibody or fragment of the invention preferably has an affinity ($K_a$) to the human cytokine of greater than $10^9 M^{-1}$. The human monoclonal antibody or fragment preferably neutralizes the activity of the human cytokine. Human monoclonal antibodies of the IgG class are particularly preferred.

Another aspect of the invention involves a human monoclonal antibody or a fragment thereof comprising at least one CDR (complementarity-determining region) of an amino acid sequence defined by amino acids 1–122 of an amino acid sequence encoded by the nucleic acid sequence shown in SEQ ID NO. 1 and/or of an amino acid sequence defined by amino acids 1–108 of amino acid sequence encoded by the nucleic acid sequence shown in SEQ ID NO. 2; or one or more somatic variants of such sequences.

A preferred embodiment of the invention relates to a human monoclonal antibody or a human IL-1α binding fragment comprising:

a $V_H$ segment having an amino acid sequence defined by amino acids 1–122 of an amino acid sequence encoded by the nucleic acid sequence shown in SEQ ID NO. 1 or by a CDR somatic variant thereof, and/or a $V_L$ segment having an amino acid sequence defined by amino acids 1–108 of an amino acid sequence encoded by the nucleic acid sequence shown in SEQ ID NO. 2 or by a CDR somatic variant thereof.

Preferably, the antibody comprises a $V_H$ segment having an amino acid sequence defined by amino acids 1–122 of an amino acid sequence encoded by the nucleic acid sequence shown in SEQ ID NO. 1 and/or a $V_L$ segment having an amino acid sequence defined by amino acids 1–108 of an amino acid sequence encoded by the nucleic acid sequence shown in SEQ ID NO. 2. More preferably, the antibody comprises $V_H$ and $V_L$ segments having the amino acid sequences defined by amino acids 1–122 of an amino acid sequence encoded by the nucleic acid sequence shown in SEQ ID NO. 1 and by amino acids 1–108 of an amino acid sequence encoded by the nucleic acid sequence shown in SEQ ID NO. 2, respectively, or comprises a CDR somatic variant of one or both of said amino acid sequences. Particularly preferred is an antibody having $V_H$ and $V_L$ segments of the amino acid sequences defined by amino acids 1–122 of an amino acid sequence encoded by the nucleic acid sequence shown in SEQ ID NO. 1 and amino acids 1–108 of an amino acid sequence encoded by the nucleic acid sequence shown in SEQ ID NO. 2, respectively, e.g., an antibody of the human $IgG_4$ isotype.

Preferred fragments of the invention comprise a $V_H$ segment having an amino acid sequence defined by amino acids 1–122 of an amino acid sequence encoded by the nucleic acid sequence shown in SEQ ID NO. 1 and/or a $V_L$ segment having an amino acid sequence defined by amino acids 1–108 of an amino acid sequence encoded by the nucleic acid sequence shown in SEQ ID NO. 2, e.g., a Fv, single-chain Fv, Fab or $F(ab')_2$ fragment. Preferably, the IL-1α binding fragment of the invention has an affinity of $10^7 M^{-1}$ or greater, more preferably of $10^8 M^{-1}$ or greater.

Another aspect of the invention involves isolated nucleic acids (DNAS) which encode a human monoclonal antibody or fragment in accordance with the present invention. Preferably, the isolated nucleic acid comprises:

a nucleotide sequence defined by base numbers 58–423 of SEQ ID NO. 1 or by a CDR encoding somatic variant thereof, or a functional equivalent of such a nucleotide sequence, and/or a nucleotide sequence defined by base numbers 67–390 of SEQ ID NO. 2 or by a CDR encoding somatic variant thereof; or a functional equivalent of one or both of said nucleotide sequences.

In a preferred embodiment, the isolated nucleic acid comprises a nucleotide sequence defined by base numbers 58–423 of SEQ ID NO. 1 and/or base numbers 67–390 of SEQ ID NO. 2.

Still other aspects of the invention relate to a pharmaceutical composition comprising at least one human monoclonal antibody or fragment in accordance with the invention and a pharmaceutically acceptable carrier, and to the use of an anti-IL-1α HuMAb or IL-1α binding fragment of the invention to treat inflammation.

The invention also includes a method for screening a solution for a desired human monoclonal antibody against a human protein comprising (1) contacting the solution with labeled protein and polyclonal or monoclonal anti-human Ig (i.e., anti-IgA, IgD, IgE, IgG and/or IgM) coupled to a substrate or with labeled protein and protein G coupled to a substrate; and (2) determining if a desired human monoclonal antibody is present in the solution by detecting labeled protein in any immunoprecipitated product.

Preferably, the solution is a collection of supernatants from a human B cell mixture. In a preferred embodiment, the solution is screened using either polyclonal or monoclonal anti-human Ig coupled to a substrate or with protein G coupled to a substrate. These screening methods can be used to prepare and identify a purified mixture of human B cells or a single human B cell clone by the steps of serially diluting a human B cell mixture giving a positive result in the screen to provide a purified mixture of human B cells or single B cell clones; culturing said purified mixture of human B cells or single human B cell clones; and screening supernatants from said cultured purified mixture of human B cells or single B cell clones by the above methods to determine if the desired human monoclonal antibody is present in the supernatants of said cultured purified mixture of human B cells or single B cell clones.

Still another aspect of the invention involves a method of producing a cDNA library enriched in DNA encoding a $V_H$ and/or $V_L$ chain of a human monoclonal antibody against a desired antigen comprising the steps of:

producing a CD40-crosslinked and EBV-transformed, immortalized and/or activated B cell population containing immortalized and/or activated B cells expressing said human monoclonal antibody;

cloning subpopulations of said immortalized and/or activated B cell population and identifying a subpopulation which contains immortalized and/or activated B cells expressing said human monoclonal antibody;

preparing a cDNA library using the mRNA from said subpopulation to create a repertoire of DNAs encoding at least the $V_H$ and/or $V_L$ chain of the human monoclonal antibodies expressed by said subpopulation of immortalized and/or activated B cells.

Preferably, this method further comprises:

identifying DNA within said library that encodes at least the $V_H$ and/or $V_L$ chain of the desired human monoclonal antibody; and using said DNA to produce a human monoclonal antibody against the desired antigen or an antigen-binding fragment of such an antibody.

In one such embodiment, a population or subpopulation which contains immortalized and/or activated B cells expressing said human monoclonal antibody is identified by the screening method described above.

Preferably, the repertoire of DNAs is incorporated into vectors capable of displaying said $V_H$ and/or $V_L$ chain on the surface of a host cell, host cells are transformed with said vectors, and host cells that display a $V_H$ and/or $V_L$ chain that binds to the desired antigen are identified by affinity binding to the desired antigen. The DNAs that encode said $V_H$ and $V_L$ chains that bind to the desired antigen can then be operatively linked to DNA encoding any necessary constant-region chains for a human immunoglobulin so as to create a DNA sequence encoding a heavy chain of a human monoclonal antibody against the desired antigen and a DNA sequence encoding a light chain of a human monoclonal antibody against the desired antigen.

Other important aspects of the invention include (1) a human B cell line established by EBV-transformation and CD40-crosslinking, which established cell line (preferably an antibody-producing clone) produces a human monoclonal antibody against a human cytokine, and (2) a process for making a human monoclonal antibody against a human cytokine comprising the steps of establishing an immortalized and/or activated human B cell population from a patient having antibodies that bind to the human cytokine, said immortalization and/or activation comprising infecting the B cells with Epstein-Barr virus and crosslinking the CD40 of such B cells;

culturing said immortalized and/or activated B cells;

isolating multiple clones from such immortalized and/or activated B cells, each of which clones secretes a human monoclonal antibody that binds to the cytokine; and using one or more of such clones to produce one or more human monoclonal antibody or a fragment thereof.

In this process nucleic acid encoding the human monoclonal antibody or fragment is preferably used to produce the desired antibody or fragment. Alternatively, the clone produced in the process is hybridized with a myeloma or heteromyeloma cell to produce a hybridoma that proliferates in culture and produces the desired antibody.

BRIEF DESCRIPTION OF THE DRAWINGS

FIGS. 6A and 6B are graphical representations showing the EL4/CTLL proliferation (cpm×10$^{-3}$) in the presence of rabbit anti-IL-1β, rabbit anti-IL-1α, or two concentrations of HuMAb X3 versus the amount of paraformaldehyde-fixed (PFA-fixed) Monocytes per well without and with LPS stimulation, respectively, in the assay "Inhibition of Membrane Associated Human IL-1α Activity" described below.

FIGS. 7A, 7B, 7C and 7D are graphical representations showing the production of IL-6 (ng/ml) in the presence of CTL IgG$_4$/κ, IL-1Ra or HuMAb X3 versus the amount of Monocytes/well, PFA-monocytes/well, LPS-Monocytes/well and PFA/LPS-Monocytes/well, respectively, in the assay "Inhibition of IL-6 production in cocultures of synoviocytes and monocytes" described below.

DETAILED DESCRIPTION OF THE INVENTION

Figure 1:
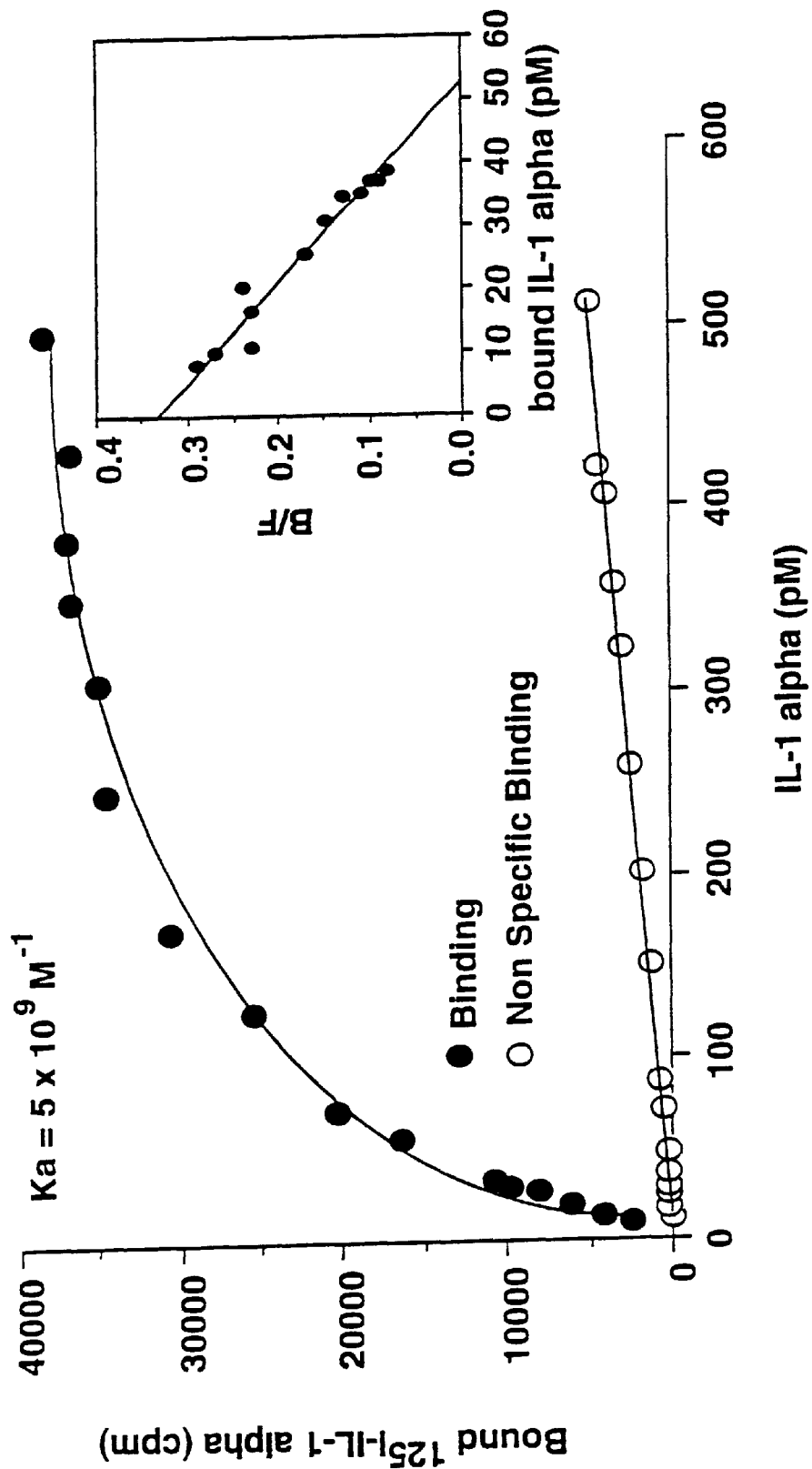
FIG. 1 is a graphical representation showing the amount of bound $^{125}$I-IL-1α (cpm) versus the concentration of IL-1α (pM) in the assay "X3 Affinity for Human IL-1α" described below.

The invention may employ a B cell population including resting B cells which retain their surface bound immunoglobulin and/or activated B cells which secrete HuMAbs. If desired, the B cell population may be sorted to select for activated B cells or for resting B cells, e.g., as described below and in WO 91/09115.

A starting human B cell population for use in providing a human anti-cytokine HuMAb (or a subsequence thereof that binds to the cytokine) in accordance with the present invention can be identified by means conventional in the art, e.g., by the methods described in the articles listed in the Section "Background of the Invention" above. A small amount of blood can be taken from patients and tested for Ig against the desired cytokine, e.g., by ELISA, radioimmunoprecipitation assay, western blotting, etc. Patients who react positively are sources of B cells that can be used to immortalize and isolate a clone producing the desired HuMAb as described further below. A larger sample for cloning can then be taken from each patient identified by the above procedures.

Suitable sources of B cells from a selected patient include peripheral blood, tonsils, adenoid tissue, spleen (in the case of removal for another medical necessity) or any other source of B cells from the body. Typically, peripheral blood is employed as the B cell source.

The blood is first treated to separate the peripheral blood lymphocytes (PBLs) from the red blood cells and platelets by means conventional in the art. For example, the peripheral blood may be diluted with an appropriate isotonic medium, e.g., RPMI 1640 medium (cat. 041-01870 M. Gibco, USA). The diluted blood is loaded onto a suitable separation medium such as FICOLL™ (available from Pharmacia, Sweden). After centrifugation, the PBLs may be aspirated from the interface between the plasma and the FICOLL™. The purified PBLs may be frozen in liquid nitrogen for later use. The plasma is then analyzed by conventional techniques such as radioimmunoprecipitation assay, ELISA, western blotting, etc., to confirm the presence of significant amounts of the desired antibody (e.g., IgG$_1$, IgG$_2$, IgG$_3$, IgG$_4$, IgA, IgD, IgM and/or IgE antibody) against the cytokine of interest.

The purified PBLs may be used directly or may be further enriched and/or sorted as discussed below. For example, T-cells may be removed by resetting with 2-aminoethylisothiouroniumbromide-treated sheep erythrocytes. Further selection for an antigen-specific B cell subpopulation can be carried out by a variety of techniques including panning, immunoadsorbent affinity chromatography, fluorescent-activated cell sorting (FACS), etc. These techniques are described for example in Casali et al., *Science*, 234:476–479 (1986); U.S. Pat. No. 4,325,706; and Mage, Hubbard et al., Parks et al. and Haegert, in *Meth. Enzymol.*, 108:118–124, 139–147, 197–241 and 386–392 (1984), respectively. The PBLs may also be treated with magnetic beads whose surface is coated with a material to selectively sort the desired B cells. Such beads may be coated, e.g., with anti-Ig isotype for the desired Ig to be separated, with anti-surface antigen to select for non-naive B cells, or with a purified cytokine.

The resulting enriched and/or sorted B cell population is then subjected to the B-cell immortalization and/or activation process described in WO 91/09115. Briefly, the B cells are transformed with Epstein-Barr virus (EBV) and their CD40 molecules are crosslinked. Reference is made to WO 91/09115 for the variations that may be employed in this activation/immortalization process.

The treated B cell population may be washed by an appropriate isotonic medium (e.g., with RPMI 1640), pelleted and then resuspended in medium. The cells are then transformed with EBV by the addition of a suitable EBV strain, preferably a strain such as the one released by the B95.8 cell line available from the ATCC (ATCC CRL 1612). The amount of EBV used may vary depending on the strain of the virus and the number of B cells to be transformed. For example, with a sample containing $14 \times 10^6$ non-sorted PBLs, 200 µl of a suspension of a concentrated EBV (strain B95.8) is typically used. Incubation with the virus is typically carried out for about 1 to 24 hours, preferably for about 2 hours, at 37° C.; but other conditions may be employed, if desired.

The EBV-infected cells are preferably washed and resuspended in an appropriate enriched medium such as Yssel's modified Iscove's medium 15% Fetal Calf Serum (FCS) [Yssel et al., *J. Immunol. Methods*, 72:219–227 (1984)]. The concentration of the PBLs in the suspension may vary depending, for example, on whether a sorting step for antigen-specific B cells was performed as described above. Lower concentrations can be employed when PBLs have been enriched in the desired B cells. Typical concentrations for non-selected PBLs are from about $1 \times 10^3$ to about $5 \times 10^4$ cells/ml. If the B cell population is first sorted as discussed above, the concentration may be decreased depending upon the efficiency of the sorting, e.g., up to about $1 \times 10^2$ cells/ml.

An agent capable of crosslinking CD40 antigen is added to the suspended cells. The crosslinking agent may include T-cells, other transfected cells expressing CD40 ligand, or membranes therefrom. Other suitable agents are described in WO 91/09115. Preferably, the agent is an immobilized monoclonal antibody specific for the CD40 antigen, e.g., immobilized on irradiated fibroblasts expressing the human or murine Fc-gamma receptor (ATCC CRL 10680).

The monoclonal antibody to CD40 can be any which binds to the CD40 marker on the B cells of the suspension and also to the Fc-gamma receptor of the L-cells. Preferably, the monoclonal antibody is selected from MAb 89 and G28-5. These antibodies are described in Valle et al., *Eur. J. Immunol.*, 19:1463–1467 (1989) and Ledbetter et al., *J. Immunol.*, 138:788–794 (1987), respectively. The hybridoma corresponding to MAb 89 has been deposited with the European Collection of Animal Cell Cultures, PHLS Center for Applied Microbiology and Research, Porton Down, Salisbury Wilts. SP4 OJG, U.K. under accession No. 89091401.

Typically, the PBLs, the CD40 antibody and the L-cells are simply mixed together in appropriate amounts. The CD40 antibody may be present in a concentration of from about 0.01 µg/ml to about 50 µg/ml, preferably from about 0.1 µg/ml to about 5 µg/ml, more preferably about 0.5 µg/ml.

The treated cell suspension is divided among an appropriate number of wells of a tissue microplate to provide a suitable cell concentration for amplification and screening. If enriched suspensions are employed as the result of an antigen-selective screening as discussed above, fewer cells per well may be used.

Typically, the initial culture phase takes 10–20 days in the case of non-selected PBLs and 5 days or even less in the case of an antigen-specific enriched B cell population, which would allow an earlier detection of specific antibodies. During this phase, fresh medium is added as necessary. The duration of this initial culture phase is adjusted to allow detection of the antigen-specific B cells, while preventing them from being overgrown by non-specific B cells. A sample of supernatant from each well is screened by an appropriate assay for the desired HuMAb positive characteristics, e.g., by radioimmunoprecipitation assay, ELISA, western blotting, etc.

In a preferred screening method, supernatants are contacted with a labeled protein (e.g., radiolabeled with $^{125}$I) and polyclonal or monoclonal anti-human Ig coupled to a substrate or insoluble support. The anti-human Ig can be a mixture of isotypes (i.e., $IgG_1$, $IgG_2$, $IgG_3$, $IgG_4$, IgA, IgD, IgE and/or IgM) or an individual isotype (e.g., $IgG_4$). Alternatively, if one is screening for an IgG HuMAb, the supernatants can be contacted with a labeled protein and protein G coupled to a substrate or insoluble support. The presence of the desired HuMAb is determined by detecting labeled protein in the immunoprecipitated product. The immunoprecipitation screens (with anti-human Ig and with protein G) may be employed serially.

Cell lines which test positive for the desired HuMAb characteristics are cloned (3–10 cells/well) and subcloned (0.5–1.0 cells/well) by techniques well-known in the art, e.g., by culturing in limiting dilution conditions for 7–20 days in additional medium as needed. Supernatants of the clones are screened by the procedures described above.

Positive clones are expanded in a larger volume and amplified by conventional incubation.

HuMAb can be purified from the supernatant of the amplified clones by conventional immunoglobulin-purification methodology. For example, the HuMAb may be precipitated with solid ammonium sulfate, reconstituted in sterile water, and dialyzed extensively against a buffer such as phosphate-buffered saline (PBS). The dialysate may then be applied to an immunoaffinity column, e.g., a column having anti-human Ig or Protein G covalently coupled to Sepharose. After washing, the desired HuMAb may be eluted from the column by any appropriate eluent, e.g., acidic buffer, chaotropic agents, etc. [for example, see Current Protocols in Immunology, edited by John E. Coligan et al., John Wiley and Sons, New York].

By the term "human monoclonal antibody" as used herein, we mean to include HuMAbs that are isolated from human B cells as discussed above (e.g., whether the antibody is prepared by culturing the immortalized and/or activated human B cells or recombinantly from human B cell cDNAs encoding such a HuMAb and whether or not the antibody is bound to a molecule which can alter its biological activity, e.g., a receptor or ligand, an enzyme, a toxin, a carrier, etc.) and antibodies that are made by recombining the variable portions of a HuMAb of the present invention of one isotype (e.g., an $IgG_4$) with the constant region of a human antibody of another isotype (e.g., a human $IgG_1$, $IgG_2$, $IgG_3$, $IgG_4$, IgA, IgD, IgM or IgE). Recombinant methods for making these HuMAbs are described below.

By the terms "fragment" or "subsequence" of a HuMAb of the present invention, we mean an antibody fragment such as an Fab, $F(ab')_2$, Fv, single-chain binding protein, or any other binding polypeptide which contains one or more complementarity determining regions (CDRs) of the variable region of a light or heavy chain of a HuMAb of the present invention (e.g., an Fab, Fv, CDR, etc. of a HuMAb in accordance with the present invention either alone or linked to any desired molecule which can alter its biological activity, e.g., a receptor or ligand, an enzyme, a toxin, a carrier, etc.). These fragments can be prepared by well-known methods. For example, fragments can be made from the full-length HuMAb protein, e.g., by papain or pepsin cleavage, or by chemical oxidation, followed by separation of the resulting fragments. Alternatively, recombinant DNA technology may be used. For example, cDNA encoding the variable regions of both heavy and light chains may be engineered to produce the Fv portion of the HuMAb of the invention. See, for example, the methodology of U.S. Pat. No. 4,642,334 which may be employed.

By the terms "CDR somatic variant" and "CDR encoding somatic variant" as used herein we mean an amino acid or nucleic acid sequence corresponding to SEQ ID NO. 1 and/or SEQ ID NO. 2 or a subsequence of SEQ ID NO. 1 and/or SEQ ID NO. 2 containing at least one CDR or CDR-encoding region thereof, but having at least one mutation, addition and/or deletion in one or more of the CDRs or CDR-encoding region of the sequence or subsequence, such that an anti-IL-1α human monoclonal antibody including said at least one mutation, addition and/or deletion has an IL-1α binding affinity of $10^8 M^{-1}$ or greater, preferably $10^9 M^{-1}$ or greater.

By the term "affinity" as used herein, we mean the measure of the binding strength between an antigenic determinant and an antigen binding site of a human monoclonal antibody of the invention or a fragment thereof as measured by the affinity constant (Ka), e.g., by the method described below.

By the term "$V_H$ segment" as used herein, we mean the variable region of the heavy chain of a human monoclonal antibody of the invention.

By the term "$V_L$ segment" as used herein, we mean the variable region of the light chain of a human monoclonal antibody of the invention.

By the term "Fv fragment" as used herein, we mean an antigen binding fragment of an antibody that contains the variable regions of the heavy ($V_H$) and light ($V_L$) chains. Those $V_H$ and $V_L$ regions can be linked to form a single-chain Fv (scFv).

By the term "Fab fragment" as used herein, we mean the antigen binding fragment resulting from the digestion with papain of a human monoclonal antibody of the invention.

By the term "$F(ab')_2$ fragment" as used herein, we mean the antigen binding fragment resulting from the digestion with pepsin of a human monoclonal antibody of the invention.

By the term "functional equivalent" as used herein, we mean a nucleic acid sequence that encodes the same amino acid sequence as the identified nucleic acid sequence.

The terms "activated" B cell and "activation" of a B cell as used herein indicate a human B cell that has been CD40 crosslinked and EBV-transformed and expresses and secretes human antibodies.

The B cell clones of the invention may be used in conventional DNA recombinant methods to produce the HuMAbs of the invention or fragments thereof. For example, RNA from the B cell clones may be isolated according to the single-step method described by (Chomczynski et al., *Anal. Biochem.*, 162 156–9 (1987). Briefly, about $10^7$ cells are lysed in guanidinium thiocyanate denaturing solution. After acidification of the mixture with 2M sodium acetate, pH4, RNA is extracted with phenol and chloroform/3-methyl-1-butanol. RNA is then precipitated with isopropanol, the RNA pellet is redissolved in denaturing solution, reprecipitated with isopropanol, and washed with 75% ethanol.

cDNA is obtained by reverse transcription, e.g., using the Superscript Reverse Transcriptase Kit (cat. 20898 BRL, Gaithersburg, Md., USA), with oligo $dT_{12-18}$ primers (Cat. 27.7858-01, Pharmacia, Uppsala, Sweden). The cDNA is then used as template in a polymerase chain reaction (PCR). The primers may be designed to include restriction sites, to allow for the directional cloning of the PCR products. For the heavy chain, primers specific for the leader sequence of all the different human $V_H$ families are used individually in conjunction with primers located at the 3'-end of the constant region corresponding to the isotype previously determined by isotyping the HuMAb by ELISA or other appropriate method (e.g., radioimmunoprecipitation assay, etc.). The light chain is amplified with individual combinations of primers corresponding to the 3'-end of the kappa or lambda chain in conjunction with a series of primers annealing to the leader sequence of the V kappa or the V lambda genes. Thus, full-length heavy and light chains starting at the initiation codon in the leader sequence and ending at the stop codon may be generated.

After appropriate restriction cleavage, both full-length heavy chains and lull-length light chains can then be cloned in any appropriate expression vector designed to be compatible with the restricted PCR products. Appropriate vectors include for example baculovirus vectors and plasmids compatible with CHO cells or other host cells. Examples of suitable vectors and hosts are described in the review "Engineered antibody molecules" in *Immunol. Reviews*, 130 (1992). Heavy and light chains can be cloned individually in distinct vectors, or in tandem in one vector. The recombinant plasmids or viral vectors may be cloned in bacteria, and a few clones may be sequenced on both strands to check for the absence of alteration of the insert. One clone each for the heavy chain and for the light chain, or one clone containing both chains, may then be selected for expression in the appropriate host cells. Depending on the vector used, it will be introduced into appropriate prokaryotic or eukaryotic cells either by transfection or by infection. The cells expressing the recombinant HuMAb are cloned, supernatant fluid from the cultured cells is collected, and the HuMAb therein can be purified, e.g. by immunoaffinity, HPLC or any other appropriate methods.

The full-length PCR product for the heavy chain can be modified for example to replace the original heavy-chain constant region by another one, so replacing one isotype by another, e.g., replacing a human $IgG_4$ isotype by a human $IgG_1$, $IgG_2$, $IgG_3$, IgA, IgD, IgM or IgE isotype. This can be accomplished through a second PCR using as 5'-primer the $V_H$ leader specific primer, and as 3'-primer a primer annealing to the 3'-end of the $V_H$ region (e.g., $IgG_4$) and including a tail corresponding to the 5'-end of the desired constant region (e.g., IgG$_1$, IgG$_2$, etc.) cloned in an appropriate plasmid. After amplification, the DNA generated encoding the heavy chain may be digested with appropriate enzymes and ligated into the new expression vector, which will now contain the sequence of the desired heavy chain. This will allow the production of a recombinant HuMAb with the variable region of the originally isolated HuMAb (e.g., the variable region from an IgG$_4$ HuMAb) and the constant region of a different human isotype (e.g., the constant region of a human IgG$_1$, IgG$_2$, etc.). This type of recombinant HuMAb will have the characteristic binding of the IgG$_4$ HuMAb, but will be able to display the effector functions normally associated with the human IgG$_1$, IgG$_2$, etc. isotype. The same method can be used to replace an isotype other than IgG$_4$ by another different isotype.

Hybridomas may also be made with the B cells of the invention by techniques conventional in the art. For example, the B cells of the invention may be fused with an appropriate myeloma cell or with a heterohybridoma cell to increase or stabilize the immunoglobulin secretion; see for example Kudo et al., *J. Immunol. Methods*, 145:119–125 (1991); Zanella et al., *J. Immunol. Methods*, 156:205–215 (1992); and Darveau et al., *J. Immunol. Methods*, 159: 139–143 (1993).

The HuMAbs and fragments of the present invention may be used therapeutically to treat existing symptoms associated with the antigen of interest. For example, IL-1α, IL-1β and TNF-α are identified as inflammatory cytokines and thus HuMAbs to such cytokines or fragments of such HuMAbs may be useful for treating inflammation including chronic or acute inflammatory reactions such as rheumatoid arthritis, osteoarthritis, inflammation associated with asthma, inflammatory bowel disease, regulating fever associated with inflammation, pain relief in inflammation, etc. For example, bowel diseases may benefit from a treatment with an anti-IL-1α HuMAb of the invention, e.g., HuMAb X3, since anti-IL-1α antibodies abolished the crypt hyperplasia in the jejunum of mice suffering from graft-versus-host disease enteropathy: see Mowat et al., *Immunology*, 80:110–115 (1993). Also, since IL-1α has been suspected to play a role in psoriasis [see Romero et al., *J. Invest. Dermatol.*, 93:518–522 (1989)], an anti-IL-1α HuMAb of the invention may be useful in treatment of psoriasis. Allergy may be another target for an anti-IL-1α HuMAb of the invention at both the regulatory and effector levels. At a regulatory level, IL-1 has been shown to be involved in the differentiation of naive T lymphocytes into TH$_2$ T cells. At the effector level, clinical trials with soluble IL-1 receptor have shown a striking inhibition of wheal and flare reaction in allergen-challenged allergic patients. Furthermore, the anti IL-1 HuMAbs and anti IL-1-binding fragments of the present invention are antagonists to IL-1 and therefore will be useful for the same indication as other known IL-1 antagonists, which either are in clinical trials for or have been shown in the literature to be useful in models of septic (endotoxin) shock, experimental autoimmune encephalomyelitis, cerebral malaria, graft-versus-host disease and chronic myelogenous leukemia [see, for review, Dinarello, *Immunol. Reviews*, 127:119–146 (1992); and Dinarello et al., *N. Engl. J. Med.*, 328:106–113 (1993)]. Finally, IL-1α has been reported to act as an autocrine growth stimulator for human thyroid and gastric carcinoma cells [Ito et al., *Cancer Res.*, 53:4102–4106 (1993)], as well as adult T cell leukemias [Shirakawa et al., *Cancer Res.*, 49:1143–1147 (1989)]. Thus, an anti-IL-1α HuMAb of the invention may be useful in the treatment of tumors.

Further examples of the utilities of other antagonists of and/or antibodies to other cytokines are described in Henderson et al., *TiPS*, 13:145–152 (1992) and in Mire-Sluis, *TIBTECH*, 11:74–77 (1993). The HuMAbs and fragments of the present invention may also be used prophylactically to prevent or inhibit the occurrence of such symptoms associated with the antigen of interest.

The HuMAbs of the invention may be particularly useful, e.g., in treating chronic diseases, in view of the long half-lives of HuMAbs (e.g., about 21 days [Adair, *Immunol. Reviews*, 130:5–40 (1992)]) compared to other cytokine antagonists (about 30 minutes for IL-1 receptor antagonist [Granowitz et al., *Cytokine*, 4:353–360 (1992)]). This longer half life may allow a bimonthly or monthly administration of the HuMAb.

The HuMAb or fragment thereof of the present invention may be used alone or in combination with at least one other HuMAb or fragment to form a cocktail or with another antiinflammatory drug. For example, such a cocktail may include two or more of the HuMAbs of the invention, each of which binds to one or more epitopes on a cytokine of interest. When such a cocktail is employed, the proportions of the various HuMAbs or fragments may vary depending, for example, upon their binding characteristics.

The HuMAbs and fragments of the present invention are preferably administered in the form of a pharmaceutical composition containing a therapeutically or prophylactically effective amount of at least one such HuMAb or fragment in combination with a pharmaceutically acceptable carrier. Any appropriate carrier may be employed, i.e., a compatible, non-toxic material suitable for delivery of the HuMAb or fragment in the desired dosage form, e.g., oral, parenteral (subcutaneous, intramuscular or intravenous), or topical dosage forms. Suitable carriers include sterile water, sterile buffered water, sterile saline, etc. Special pharmaceutical compositions to insure a sustained release of the HuMAb and/or fragment may also be employed.

The concentration of the HuMAb or fragment of the invention in the pharmaceutical compositions may vary, e.g., from about 0.1 μg/ml to about 1 mg/ml, preferably from about 1 μg/ml to about 100 μg/ml. The concentration used will depend upon the number of HuMAbs and/or fragments thereof employed in the composition, their binding characteristics and the dosage form selected. The dose will be adjusted in a conventional manner by the skilled artisan to levels appropriate to achieve the desired result in vivo.

As mentioned above, the HuMAbs and/or fragments of the invention can be used prophylactically or therapeutically. Thus, the agent may be administered before the onset of symptoms or after the symptoms have appeared. The HuMAbs and/or fragments of the invention will be administered in a dose effective to provide the desired alleviation of symptoms. Amounts effective for this purpose will depend upon many factors, e.g., the severity of the symptoms in the patient.

The HuMAb or fragment of the invention may be administered in dosages of from about 0.001 μg/kg to about 1 mg/kg, e.g., about 0.01 μg/kg to about 1 μg/kg, preferably from about 0.01 μg/kg to about 0.1 μg/kg. The proper dosage of a HuMAb or fragment of the invention for a particular situation will be determined by using common practices in the art. Generally, treatment may be initiated with smaller dosages that are less than the optimum dose of the agent. Thereafter, the dosage may be increased by small amounts until the optimum effect under the circumstances is reached. The amount and frequency of administration of the HuMAb or fragment of the invention will be regulated according to the judgment of the attending clinician considering such factors as age, condition and size of the patient as well as severity of the symptoms being treated.

The HuMAbs and fragments of the invention may also be used for diagnostic purposes in the same manner as other antibodies and fragments are currently used in the art. For example, the HuMAbs and fragments of the invention can be used in assays for the cytokine to which they bind or in an immunopurification procedure to isolate an antigen to which they bind. The HuMAbs and fragments may be used either labeled (e.g., with a radioisotope, fluorescent group, enzyme or other appropriate ligand) or unlabeled, as is conventional in the art for the particular assay of interest (e.g., in a sandwich assay with a second labeled antibody). The HuMAbs and fragments may be used in agglutination assays, enzyme immunoassays, etc. They could for example be used to calibrate a dosage of cytokine-specific IgG in the serum or in any other biological fluid. Thus, the labeled or unlabeled forms of the HuMAbs and fragments of the invention may be employed as elements of kits for purposes of performing the desired assay.

The invention disclosed herein is illustrated by the following Examples, which should not be construed to limit the scope of the disclosure. Alternative methods within the scope of the invention will be apparent to those skilled in the art.

Unless otherwise indicated, percentages for solids in solid mixtures, liquids in liquids, and solids in liquids are weight/weight, volume/volume and weight/volume, respectively.

EXAMPLES

General Methods and Reagents

Recombinant human IL-1 alpha (IL-1α) and recombinant human IL-1 Receptor antagonist (IL-1Ra) were expressed in *E. coli* by standard methods and purified by ion-exchange and gel chromatographies.

Recombinant human IL-1 beta (IL-1β) was purchased from Genzyme (Boston, Mass.).

$^{125}$I-labeled recombinant human IL-1α (specific activity: 1200–2200 Ci/mmole) was from Du Pont De Nemours (Wilmington, Del.).

Mouse monoclonal antibody to human IL-1α and rabbit neutralizing antibodies against human IL-1α and human IL-1β were from Genzyme (Cambridge, Mass.).

Protein G (from Group C Streptococcus sp.) coupled to Sepharose 4B™, and anti-human Ig polyvalent immunoserum (IgG fraction) coupled to agarose were obtained from Sigma Chemical Co. (St Louis, Mo.).

Tissue culture media, fetal calf serum (FCS), L-glutamine, Hepes buffer, and Phosphate Buffered Saline (PBS) were from GIBCO (Paisley, UK). Bovine serum albumin (BSA) was from Sigma Chemical Co. and gentamycin from Schering-Plough (Levallois-Perret, France).

The murine thymoma cell line EL4 (ATCC, TIB 181) was maintained in RPMI 1640 supplemented with 10% FCS, 2 mM L-glutamine, 50 µg/ml gentamycin and $5\times10^{-5}$M 2-mercaptoethanol (2-ME) in a humidified 37° C. chamber with 5% $CO_2$.

The murine IL-2-dependent cytotoxic T cell line (CTLL-2) (ATCC, TIB 214) was maintained in RPMI 1640 supplemented with 10% FCS, 2 mM L-glutamine, 50 µg/ml gentamycin, $5\times10^{-5}$M 2-ME and 20 U/ml recombinant human IL-2 in a humidified 37° C. chamber with 5% $CO_2$.

Human synoviocytes were isolated from rheumatoid synovial biopsies obtained from rheumatoid arthritis patients undergoing knee or wrist synovectomy, or joint replacement as described in Dechanet et al., *J. Immunol.*, 151:4908–4917 (1993). Fat and fibrous tissues were removed. The resulting fragments of synovium were finely minced into small pieces and digested with 4 mg/ml collagenase (Worthington, Freehold, N.J.) in PBS for 2–3 hours at 37° C. After centrifugation, cells were resuspended in α-MEM (Gibco) medium [Minimum Essential Medium Eagle] supplemented with 2 mM L-glutamine, 20 mM Hepes buffer, 10% FCS and 50 µg/ml gentamycin. Cells were cultured in 100 mm culture Petri dishes, in humidified 5% $CO_2$ atmosphere. After adherence for 48 hours, non-adherent cells were removed and adherent cells were cultured until confluence. Then cells were cultured in 150 cm$^2$ culture flasks after trypsin treatment. Synoviocytes were used from passage 3 to passage 8. They were negative for the expression of CD1, CD2, CD3, CD19, CD14 and HLA-DR as determined by flow cytometry analysis on a FACScan (Becton Dickinson, Sunnyvale, Calif.) after staining with specific fluorescein-isothiocyanate (FITC) conjugated monoclonal antibodies (mAbs) (Becton Dickinson, Mountain View, Calif.).

The transformant Epstein-Barr virus (EBV), strain B 95.8, was produced by culturing transformed marmoset leukocytes (ATCC, CRL 1612) essentially as described by Miller and Lipman [*Proc. Natl. Acad. Sci.* USA, 70:190 (1973)].

The ltk$^-$ transfected mouse fibroblastic L cell line (ATCC CRL 10680) stably expressing the human Fcγ receptor II (FcγRII or CDw32), and the mouse anti-human CD40 monoclonal antibody, mAb 89, were obtained as described in WO 91/09115.

Standard Immunoprecipitation Protocol with Protein G

In order to identify the presence of human antibodies (IgG) against human IL-1α in biological samples (sera, plasma, etc.) or culture supernatants, an immunoprecipitation assay was carried out using radio-labeled recombinant human IL-1α and protein G-Sepharose as precipitating reagent. This assay allowed the identification of the four sub-classes of human IgG ($IgG_1$, $IgG_2$, $IgG_3$ and $IgG_4$). Typically, 50 µl of sera/plasma from patients or 50 µl of culture supernatants (both used at appropriate dilution in PBS, 1% BSA) were incubated for 45 minutes at room temperature with 50 µl (50 pM) of human $^{125}$I-IL-1α (diluted in PBS 1% BSA) in a well of a 96-well filtration microplate MultiScreen-HA™ (Millipore Co., Bedford, Mass.) whose bottom was composed of a nitrocellulose membrane (HATF 0.45 µm). Each sample was tested in duplicate. Then, 50 µl of a dilution of protein G coupled to Sepharose 4B™ (Sigma Chemical Co) (15 ml beads diluted to 50 ml in PBS 1% BSA) were added to each well and incubated for 45 minutes at room temperature. The wells were then washed three times with PBS using a vacuum manifold (Millipore Co.), and the dried membranes were collected into appropriate vials using a special collector system (Millipore Co.). The radioactivity corresponding to the complexes $^{125}$I-IL-1α/anti-IL-1α was counted in a Wizard gamma-counter (Wallac Oy, Turku, Finland). Positive and negative controls were performed for each plate, using a rabbit anti-human IL-1α antiserum (Genzyme, Cambridge, Mass.) or an unrelated antiserum respectively. Specificity of the human $^{125}$I-IL-1α precipitation obtained with the tested samples was further confirmed through its inhibition by preincubation of those samples with a 100-fold excess of unlabeled recombinant human IL-1α.

Derived Immunoprecipitation Protocols

The above standard immunoprecipitation assay has been modified in order to identify human antibodies to human IL-1α of isotypes other than IgG or to better identify the IgG subclass and light chain of such antibodies contained in patient biological fluids, e.g., sera or culture supernatants. The principle of the different assays was the same as in the standard protocol, but the precipitating reagent, e.g. protein G-Sepharose, was changed. The following reagents were used: agarose beads coupled with goat polyspecific antibodies to human IgM, IgG and IgA (Sigma Chemical Co); Affi-Gel 10™ gel (Bio-Rad laboratories, Richmond, Calif.) coupled, according to the manufacturer's instructions, with specific goat antibodies to human IgA heavy chain, human lambda light chain or human kappa light chain (Sigma Chemical Co.) or coupled with mouse mono-clonal antibodies to human IgG, heavy chain, human $IgG_2$ heavy chain, human $IgG_3$ heavy chain or human $IgG_4$ heavy chain (Calbiochem Co., La Jolla, Calif.

These protocols may be employed with other antigens of interest by substituting an appropriately labeled antigen for the $^{125}$I-IL-1α in the assays.

Detection of Human Antibodies to Human IL-1α in Human Biological Fluids

Detection of naturally occurring autoantibodies to human IL-1α in biologiical fluids, e.g., sera or plasma, was performed by using the radioimmuno-precipitation assay described above. Blood samples from healthy donors or sick patients (particularly patients suffering from autoimmune diseases, infectious diseases or neurologic disorders) were screened. 10% of the samples from healthy donors (101/1009) contained IgG antibodies to human IL-1α, in that, when diluted 1:10, they significantly precipitated $^{125}$I-labeled human recombinant IL-1α with protein G-Sepharose. Some samples also contained IgA autoantibodies to human IL-1α, as determined by immunoprecipitation of $^{125}$I-labeled IL-1α with appropriate anti-human IgA reagents coupled to beads. An increased frequency (15.9%, 59/370) of IgG anti-IL-1α autoantibodies was observed in sera of patients with autoimmune diseases. Precipitation of radio-labeled human IL-1α was specific since it was completely inhibited by pre-incubation of the positive samples with a 100-fold excess of unlabeled human IL-1α.

Autoantibodies to human IL-1α were titrated using the immunoprecipitation assay for serial dilutions of positive sera or plasma. Then, sera or plasma samples with high titers of anti-IL-1α antibodies were also tested for their ability to inhibit the binding of human $^{125}$I-IL-1α to its receptors expressed on the murine thymoma EL4 cells. Serial dilutions (in RPMI 1640, 1% BSA, 20 mM Hepes) of positive sera or plasma were pre-incubated for 1 hour at 4° C. with a fixed concentration (70 pM) of human $^{125}$I-IL-1α, in a final volume of 100 µl. Experiments were performed in conical 1 ml Eppendorf tubes or in V-bottomed microtiter plates (Nunc, Roskilde, Denmark), and each sample was tested in triplicate. Then 1×10$^6$ (100 µl) of EL4 cells in RPMI 1640, 1% BSA, 20 mM Hepes were added to each tested point and the mixures were incubated for 3 hours at 4° C. Cells were then washed and centrifuged three times at 4° C., and the radioactivity corresponding to cell-bound $^{125}$I-IL-1α was counted in a Wizard gamma-counter (Wallac). Non-specific binding was measured in the presence of a 100-fold excess of unlabeled human IL-1α. Most of the sera or plasma containing autoantibodies to human IL-1α was found to block human IL-1α binding to its receptor. Patients were selected according to these criteria. Examples of the reactivity of 5 different sera are shown in Table 1 below.

TABLE 1

Detection of IgG autoantibodies to human IL-1α in human sera

| Sera | Dilution | $^{125}$I-IL-1α precipitated with Protein G (cpm) | $^{125}$I-IL-1α bound to EL4 cells cpm | (% inhibition) |
|---|---|---|---|---|
| none | | 787 | 4516 | |
| negative | 1/5 | 1082 | 4490 | |
| C | 1/5 | 3860 | 903 | (80) |
| | 1/10 | 3844 | 2365 | (48) |
| | 1/20 | 2554 | 3233 | (28) |
| S | 1/5 | 3697 | 1685 | (63) |
| | 1/10 | 2763 | 3156 | (30) |
| | 1/20 | 2061 | 3864 | (14) |
| T | 1/5 | 3392 | 2332 | (48) |
| | 1/10 | 2692 | 2945 | (35) |
| | 1/20 | 1953 | 3559 | (21) |
| V | 1/5 | 4130 | 642 | (86) |
| | 1/10 | 3741 | 655 | (85) |
| | 1/20 | 2486 | 1976 | (56) |
| X | 1/5 | 3866 | 701 | (84) |
| | 1/10 | 3723 | 2122 | (53) |
| | 1/20 | 2593 | 2666 | (41) |

C, S, T, V, and X designate serum samples from healthy persons and patients.

In a similar manner, autoantibodies against other cytokines in human biological fluids, such as sera, plasma, etc., are detected by substituting, for example, $^{125}$I-TNF-α, $^{125}$I-IL-1β, $^{125}$I-IL-6 or $^{125}$I-IL-10 for $^{125}$I-IL-1α in the above procedure. Samples from such patients are then EBV-transformed, CD40-activated, screened and amplified by the methods described below to produce subpopulations and/or single clones of B cells producing HuMAbs against IL-1β, TNF-α, IL-6 or IL-10. Detection of IgG autoantibodies to human IL-10 in a human serum is shown in Table 2 below.

TABLE 2

Detection of IgG autoantibodies to human IL-10 in human serum

| Sera | Dilution | $^{125}$I-IL-10 precipitated with Protein G (cpm) | $^{125}$I-IL-10 precipitated after protection with unlabeled IL-10 (cpm) |
|---|---|---|---|
| none | | 405 | 375 |
| negative | 1/2 | 430 | 410 |
| positive | 1/2 | 1425 | 450 |
| | 1/4 | 1142 | 417 |
| | 1/8 | 927 | 391 |
| | 1/16 | 734 | 397 |
| | 1/32 | 442 | 401 |

Generation of X3, a Human Monoclonal Antibody to Human IL-1α

Plasma from a selected patient (identified as X) was found to precipitate human $^{125}$I-IL-1α with protein G and inhibited the binding of human $^{125}$I-IL-1α to EL4 cells in the protocols described above (see Table 1 above).

EBV Transformation and CD40 Activation of B Lymphocytes from Patient X 40 ml of peripheral blood collected on EDTA treated tubes were obtained from patient X. Blood was diluted 1:1 with PBS and loaded onto a Ficoll™ (Pharmacia, Uppsala, Sweden) density gradient. Peripheral blood mononuclear cells (PBMNC) were collected at the interface after centrifugation (30 min, 600 g). Cells were washed four times in PBS, and 39×10⁶ PBMNC were finally obtained, with a cell viability superior to 95%, as estimated by Trypan Blue dye exclusion.

The cells were pelleted and resuspended in 1 ml of RPMI complete medium which consisted of RPMI 1640 supplemented with 10% heat-inactivated FCS, 2 mM L-glutamine and 50 µg/ml gentamycin. Then, 500 µl of a 100× concentrated Epstein-Barr virus (EBV) suspension (strain B95.8) were added, and this mixture was incubated for 2 hours at 37° C. under 5% $CO_2$ in a humidified incubator. The cells were then washed once in RPMI complete medium and the pellet was resuspended at 5×10⁴ cells/ml in Yssel's modified Iscove's medium [Yssel et al., *J. Immunol. Methods* 72:219–227 (1984)] supplemented with 15% heat-inactivated FCS, 2 mM L-glutamine, 50 µg/ml gentamycin. Irradiated L cells (7,000 rads) stably expressing the FcγRII (CDw32) were added at a final concentration of 5×10⁴ cells/ml, together with the murine monoclonal anti-human CD40 antibody mAb 89 used at a final concentration of 0.5 µg/ml. 100 µl aliquots of this mixture were then distributed in each well of round-bottomed 96-well culture plates (Nunc), and the plates were incubated at 37° C. under 5% $CO_2$ atmosphere in humidified incubator. After 5 days of incubation, 125 µl of fresh culture medium containing 0.5 µg/ml anti-CD40 mAb 89 were added to each well.

Screening of Culture Supernatants

After 10 days of incubation, the culture supernatants were screened for the presence of human anti-IL-1α antibodies. Thus, 60 µl of culture medium were collected from each well, and the 12 different supernatants corresponding to the 12 wells of each line of the culture plates were pooled in one microtube. This operation was facilitated by the use of a BIOMEK 1000 work station (Beckman Instruments, Fullerton, Calif.). Then, 50 µl of the pooled supernatants were screened individually for the presence of antibodies that bind human IL-1α by immunoprecipitation of recombinant human $^{125}$I-IL-1α with polyspecific anti-human IgM, IgA and IgG antibodies coupled to agarose (Sigma Chemical Co). A total of 13 positive pools were identified with this screening assay. A positive result was immediately confirmed by immunoprecipitation of human $^{125}$I-IL-1α with protein G coupled to Sepharose, indicating the presence of human IgG antibodies to human IL-1α.

The 13 pools were then identified and split. At day 11, 50 µl of culture supernatants were harvested from each well corresponding to the 13 pools, and they were tested individually by immunoprecipitation of human $^{125}$I-IL-1α with protein G. A total of 13 different positive wells were thus identified. They were designed X1 to X13.

Characterization of the Human Antibodies to Human IL-1α from the 13 Positive Cell Lines The 13 initial positive cell lines (X1 to X13) were expanded in order to produce supernatants for further analysis, and the cells were frozen and stored in liquid nitrogen. The positive results of the 13 different lines were verified at different times by immunoprecipitation of human $^{125}$I-IL-1α with protein G.

Experiments performed with positive culture supernatants have shown that the 13 cell lines secreted human antibodies that inhibit the binding of human $^{125}$I-IL-α on EL4 cells.

The isotype of the human anti-IL-1α antibodies contained in these supernatants was determined by using an immuno-precipitation assay of human $^{125}$I-IL-1α with Affi-Gel 10 beads coated with specific antibodies against human $IgG_1$, $IgG_2$, $IgG_3$ or $IgG_4$ heavy chain, or antibodies to human kappa (κ) or lambda (λ) light chain. Of the human anti-IL-1α antibodies secreted by the 13 cell lines, three were of $IgG_1$/κ isotype, one was of $IgG_4$/λ isotype, and the nine others were of $IgG_4$/κ isotype. In particular, the human anti-IL-1α antibody X3 was of $IgG_4$/κ isotype.

In a manner similar to the above methods, B cells from 14 other patients that tested positive in the detection screen described above were also activated with CD40 and transformed with EBV, screened and expanded. PBLs isolated from these 14 selected patients were submitted to EBV infection, cultured in the CD40 system and screened as described above for patient X. 28 other B cell lines secreting anti-IL-1α antibodies were identified. Thus, among a total of 482×10⁶ PBLs used (from 15 different patients), 41 cell lines secreting anti-human IL-1α antibodies were identified; 40 secreted IgG and one secreted IgA antibodies to human IL-1α, and all these 41 cell lines precipitated $^{125}$I-IL-1α and inhibited its binding on EL4 cells. Details are shown in Table 3 below. Whereas the 40 positive wells other than the one from patient X as described above lost anti-IL-1α precipitating activity upon subsequent cloning and subcloning, the B cells in positive wells may be used to identify and isolate other anti-IL-1α HuMAbs by the other methods described below, e.g., by repertoire cloning.

TABLE 3

Generation of anti-IL-1α secreting human B cell lines

| Patient | No. PBLs (× 10⁶) | PBLs/well (× 10³) | No. positive cell lines | Anti-IL-1α Isotype | Binding Inhibition |
|---|---|---|---|---|---|
| C | 50 | 5 | 9 | IgG | + |
| D | 45 | 5 | 1 | IgG | + |
| F | 21 | 5 | 0 | — | − |
| H | 40 | 5 | 1 | IgG | + |
| I | 41 | 5 | 1 | IgG | + |
| P | 90 | 5 | 12 | IgG + IgA | + |
| Q | 20 | 5 | 0 | — | − |
| R | 15 | 4 | 1 | IgG | + |
| S | 40 | 1 | 0 | — | − |
| T | 10 | 1 | 0 | — | − |
| U | 16 | 1 | 0 | — | − |
| V | 15 | 1 | 0 | — | − |
| W | 15 | 1 | 2 | IgG | + |
| X | 39 | 5 | 13 | IgG | + |
| Y | 25 | 5 | 1 | IgG | + |
| TOTAL | 482 | | 41 | 40 IgG + 1 IgA | + + |

Cloning of the 13 Positive Cell Lines from Patient X

Twelve days after the initiation of the culture, the 13 positive initial cell lines (X1 to X13) were cloned by limiting dilution at 5 cells/well in 96-microwell plates (round-bottomed). Aliquots of cells were harvested, enumerated and resuspended at 50 cells/ml in complete culture medium containing 5×10⁴/ml irradiated (7,000 rads) CDw32 transfected L cells and 0.5 µg/ml anti-CD40 mAb 89. 100 µl of this suspension was distributed in each well and culture plates were incubated at 37° C., 5% $CO_2$. After 6 days of incubation, 125 µl of fresh Yssel's modified Iscove's medium were added to each well. Between 10 and 24 days after the cloning initiation, 50 µl of supernatant were harvested from the wells showing a cell growth, and screened individually for anti-IL-1α antibodies by the immunoprecipitation assay performed with anti-human IgM, IgA and IgG antibodies coupled with agarose or protein G-Sepharose. The cell line X3 gave rise to three positive clones: X3A, X3B and X3C.

Subcloning of X3A, X3B and X3C

The three positive clones X3A, X3B and X3C were then subcloned at 1 cell/well in complete culture medium without feeder cells. The screening was performed at different days after the initiation of the culture, by immunoprecipitation assay as described above. A total of 261 EBV-transformed cell lines secreting human anti-IL-1α antibodies were obtained. The cells were expanded in RPMI complete medium. Culture supernatants were frozen and stored at −20° C. Cells were frozen at $1 \times 10^6$ to $5 \times 10^6$ cells/ml and kept in liquid nitrogen.

Antibodies Isotyping in Conditioned Media

Three subclones: X3A-16G5, X3B-14G10 and X3C-20G10, obtained as described above, were selected and maintained in culture in RPMI 1640 supplemented with 10% FCS, 2 mM L-glutamine and 50 μg/ml gentamycin. Conditioned media from these three clones were collected and tested (dilution 1:1 in PBS, 0.05% Tween-20) in enzyme-linked immunosorbent assays (ELISA) specific for human IgM, IgG or IgA isotypes, and for human $IgG_1$, $IgG_2$, $IgG_3$ or $IgG_4$ subclasses.

Only a human $IgG_4$ immunoglobulin has been identified in conditioned media from the three selected subclones X3A-16G5, X3B-14G10 and X3C-20G10, thus suggesting the monoclonality of these three EBV-transformed cell lines. Furthermore, sensitive PCR analysis of $V_H$, $C_H$, $V_L$, and $C_L$ usage indicated the presence of a unique Ig transcript in the isolated B cell clones. The subclone X3A-16G5 was selected for subsequent analysis and the human monoclonal antibody produced by it will be referred to hereinafter as X3.

Purification of the Human Monoclonal Antibody X3

The subclone X3A-16G5 was used to produce large quantities of human monoclonal antibodies to human IL-1α. This clone was stable for more than 5 months, and was continuously amplified in RPMI 1640 medium supplemented with 10% FCS, 2 mM L-glutamine and 50 μg/ml gentamycin to allow the generation of large number of cells. Then cells were collected, washed twice in PBS to remove FCS protein contamination, and recultured for 5 days at the initial concentration of $5 \times 10^5$ cells/ml in RPMI 1640 supplemented with 2 mM L-glutamine, 50 μg/ml gentamycin and 1×Nutridoma-HU (Boeringer Mannheim GmbH, Mannheim, Germany). Under these conditions, this clone produced 3 to 5 mg/l of monoclonal $IgG_4$.

Conditioned culture medium was then collected, filtered and concentrated. Immunoglobulins were then precipitated with 2.4M $(NH_4)_2SO_4$. After centrifugation, the precipitate was dissolved in TPP buffer (20 mM $H_3PO_4$, pH 7) and loaded to an affinity column of protein G-Sepharose 4B (Sigma Chemical Co.) previously equilibrated with TPP buffer. The column was then washed once with TPP buffer, 1M NaCl, and three times with TPP buffer alone. The human antibody X3 was eluted from the column with 0.1M glycine buffer, 0.4M NaCl, pH 2.7. The pH was immediately adjusted to pH 8 by addition of TRIZMA Base 1M, pH 12, and the purified antibody was dialyzed against PBS.

The quality of the X3 purifications was verified by subjecting the obtained preparations to polyacrylamide gel electrophoresis (SDS-PAGE) in a 10% gel under reducing conditions essentially as described by Laemmli [*Nature* 227:680–685 (1970)], and after subjecting the gel to silver staining.

To verify that the human antibody X3 was not denatured during the purification, purified preparations of X3 were tested for their ability to precipitate human $^{125}$I-IL-1α in the standard assay described above using protein G-Sepha rose.

X3 Affinity for Human IL-1α

To determine the affinity of the human monoclonal antibody X3 for human IL-1α, the equilibrium association constant of X3/IL-1α complexes was measured. Purified human antibody X3 was incubated with increasing concentrations of human $^{125}$I-IL-1α (10 to 500 pM) in a final volume of 250 μl in RPMI 1640, 1% BSA, 20 mM Hepes. Each tested condition was performed in triplicate. Nonspecific binding controls were performed in duplicate by addition of 50 nM unlabeled recombinant human IL-1α. After 4 hours' incubation at 4° C., 200 μl of each sample were distributed in one well of 96-well special titration plates (MultiScreen-HA, 0.45 μm) containing 50 μl of protein G coupled to Sepharose. After 1 hour's incubation at 4° C., plates were washed four times with PBS and dried membranes were collected from each well. Radioactivity corresponding to the complexes $^{125}$I-IL-1α/anti-IL-1α/protein G-beads retained on the membranes was counted using a Wizard gamma-counter (Wallac). Specific binding of human $^{125}$I-IL-1α was calculated, then plotted versus free human $^{125}$I-IL-1α concentrations and subjected to Scatchard analysis using a Ligand software (FIG. 1).

The value of the equilibrium affinity constant $(K_a)$ obtained for the human monoclonal antibody X3 was $5 \times 10^9 M^{-1}$.

Inhibition of Human IL-1α Receptor Binding

The ability of human monoclonal antibody X3 to inhibit the binding of radiolabeled human IL-1α to IL-1 receptors expressed on murine thymoma EL4 cells was investigated using both conditioned medium and the purified antibody. Serial dilutions (in RPMI 1640, 1% BSA, 20 mM Hepes) of positive culture supernatants or purified HuMAb X3 were pre-incubated for 1 hour at 4° C. with a fixed concentration (70 pM) of human $^{125}$I-IL-1l, in a final volume of 100 μl. Experiments were performed in conical 1 ml Eppendorf tubes or in V-bottomed microtiter plates (Nunc, Roskilde, Denmark), and each sample was tested in triplicate. Then, $1 \times 10^6$ (100 μl) of EL4 cells in RPMI 1640, 1% BSA, 20 mM Hepes were added to each tested point and incubated for 3 hours at 4° C., then washed three times, and the radioactivity corresponding to cell-bound $^{125}$I-IL-1α was counted in a Wizard gamma-counter (Wallac). Non-specific binding was measured in the presence of a 100-fold excess of unlabeled human IL-1α.

Figure 2:
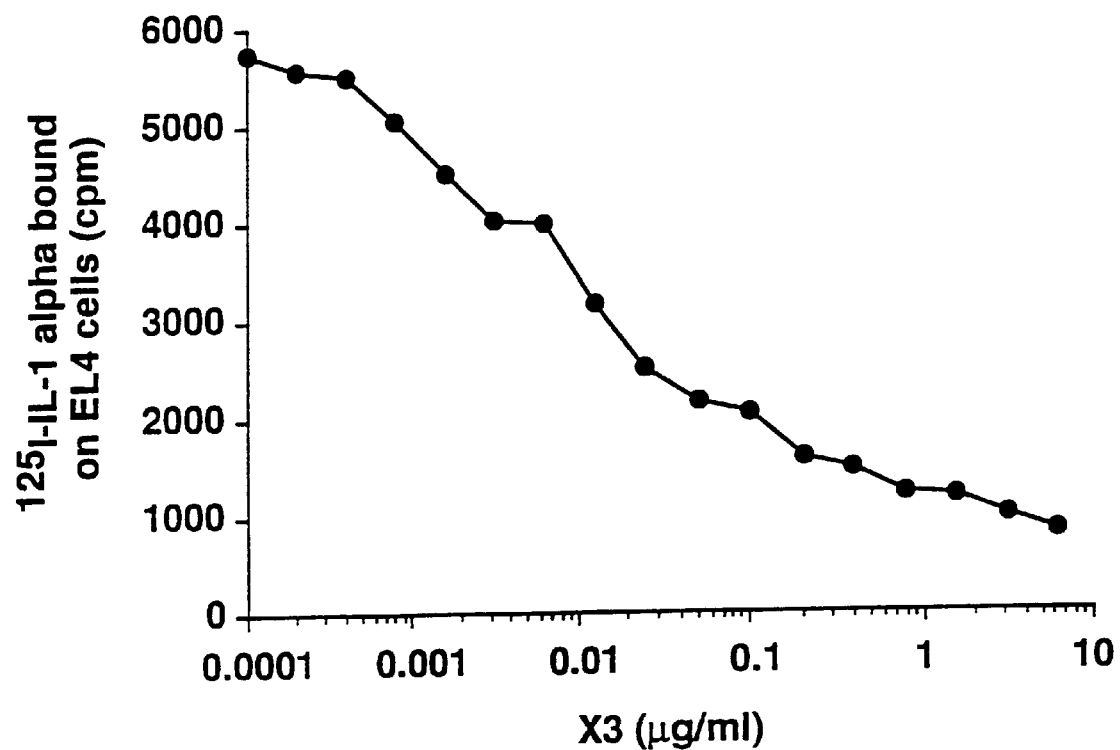
FIG. 2 is a graphical representation showing the amount of $^{125}$I-IL-1α bound on EL4 cells (cpm) versus the concentration of HuMAb X3 (μg/ml) in the assay "Inhibition of Human IL-1α Receptor Binding" described below.

The results presented in FIG. 2 indicated that the antibody X3 blocks in a dose-dependent manner the binding of radiolabeled human IL-1α on EL4 cells. The concentration of antibody X3 required to block 50% of receptor binding $(IC_{50})$ was found to be 0.015 μg/ml (100 pM) for a constant concentration of 70 pM of radiolabeled human IL-1α.

Cross-Reactivity of the Human Monoclonal Antibody X3

To determine whether antibody X3 specifically binds to human IL-1α, different preparations of IL-1 were tested for their ability to protect the precipitation of human $^{125}$I-IL-1α by the human antibody X3. Different dilutions (in PBS, 1% BSA) of purified antibody X3 were preincubated for 1 hour at room temperature without or with an excess (10 nM) of either recombinant human IL-1α (as positive control), recombinant human IL-1β or recombinant human IL-1 receptor antagonist (IL-1Ra). Then human $^{125}$I-IL-1α (50 pM) was added to each sample and reaction was incubated for 45 minutes at room temperature. Each sample was tested in duplicate in MultiScreen-HA™ plates. Precipitation of $^{125}$I-IL-1α/anti-IL-1α complexes was done with protein G coupled to Sepharose and radioactivity was counted in a Wallac Wizard gamma-counter.

Figure 3:
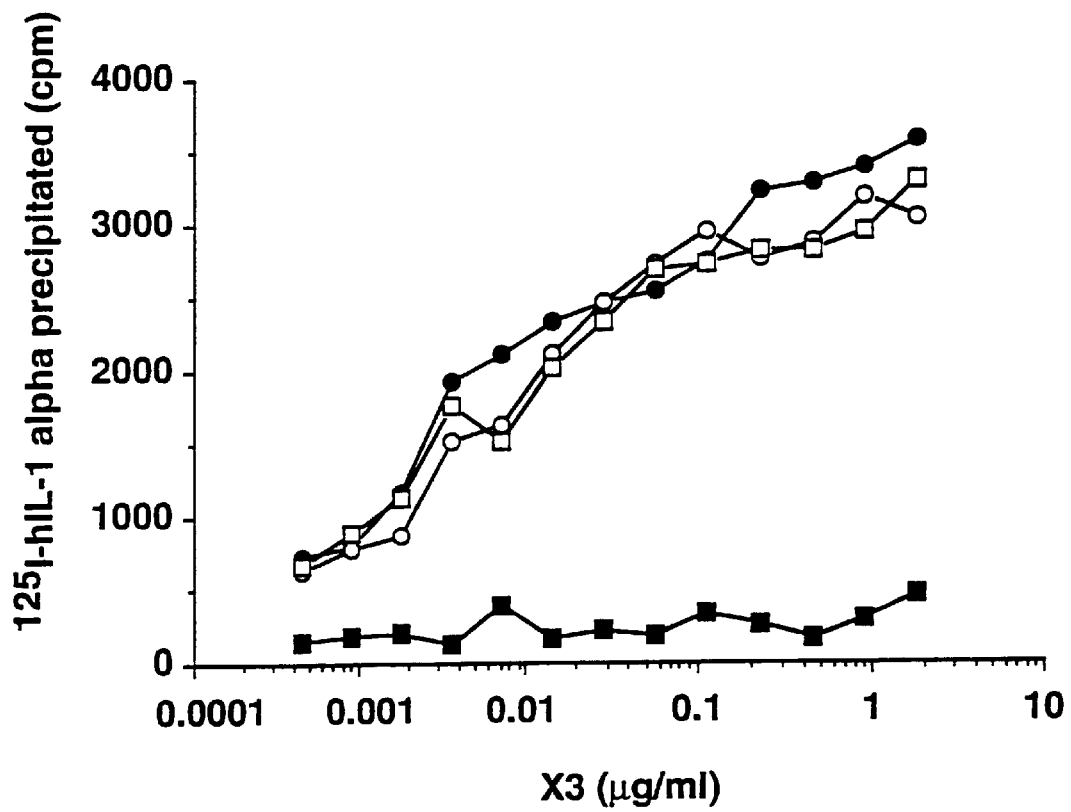
FIG. 3 is a graphical representation showing the amount of $^{125}$I-IL-1α precipitated (cpm) versus the concentration of HuMAb X3 (μg/ml) in the assay "Cross-Reactivity of the Human Monoclonal Antibody X3" described below using excess human IL-1β, human IL-1Ra or human IL-1α to protect against immunoprecipitation by HuMAb X3.

The results as shown in FIG. 3 showed that neither an excess of unlabeled human IL-1β nor an excess of unlabeled human IL-1Ra protected the immunoprecipitation of human $^{125}$I-IL-1α by antibody X3, while unlabeled human IL-1α completely inhibited radiolabeled human IL-1α precipitation. These results indicate that the human monoclonal antibody X3 specifically recognized human IL-1α, but not human IL-1β and human IL-1Ra.

Inhibition of Human IL-1α-induced IL-2 Secretion by EL4 Cells

The biological activity of human IL-1 was measured by its ability to stimulate IL-2 production by the murine thymoma subline EL4-6.1 [Zubler et al., *J. Immunol.*, 134:3662–3668 (1985)]. The IL-2 production was further determined using the CTLL-2 assay [Gillis et al., *J. Immunol.*, 120:2027–2033 (1978)]. The proliferation of IL-2-dependent CTLL cells is proportional to the concentration of IL-2 produced by EL4 cells in the first step of culture.

Different concentrations of the purified human monoclonal antibody X3 were incubated for 30 minutes at 37° C. with various concentrations of recombinant human IL-1α or human IL-1β in a final volume of 100 μl/well in flat-bottomed 96-well culture plates (Falcon, Oxnard, Calif.). Each experimental point was done in triplicate and reagent dilutions were performed in culture medium composed of RPMI 1640 supplemented with 2 mM L-glutamine, 10% heat-inactivated FCS, 50 μg/ml gentamycin and $5\times10^{-5}$M 2-ME. Then, 100 μl of a suspension of EL4 cells ($5\times10^5$ cells/ml) in culture medium containing 0.2 μg/ml ionomycin (Sigma Chemical Co) were added to each well. After 24 hours' incubation at 37° C. under 5% $CO_2$ in a humidified incubator, cell-free supernatants were harvested and tested for their IL-2 concentrations.

Figure 4A:
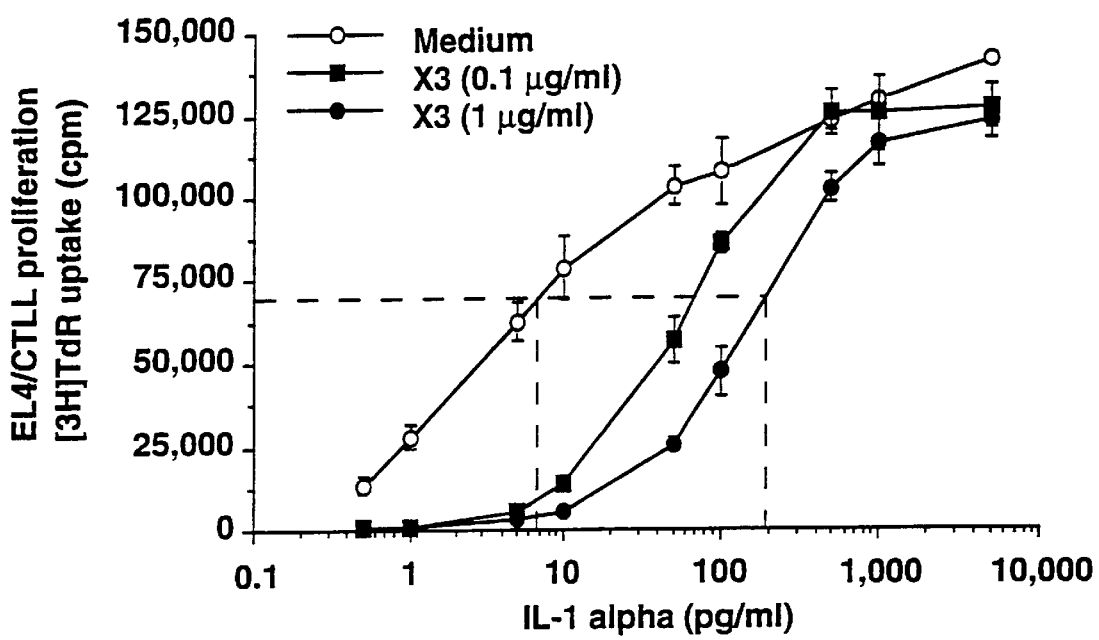
FIG. 4A is a graphical representation showing the EL4/CTLL proliferation—[$^3$H]TdR uptake (cpm) versus the concentration of IL-1α (pg/ml) in the assay "Inhibition of Human IL-1α-induced IL-2 Secretion by EL4 Cells" described below.
Figure 4B:
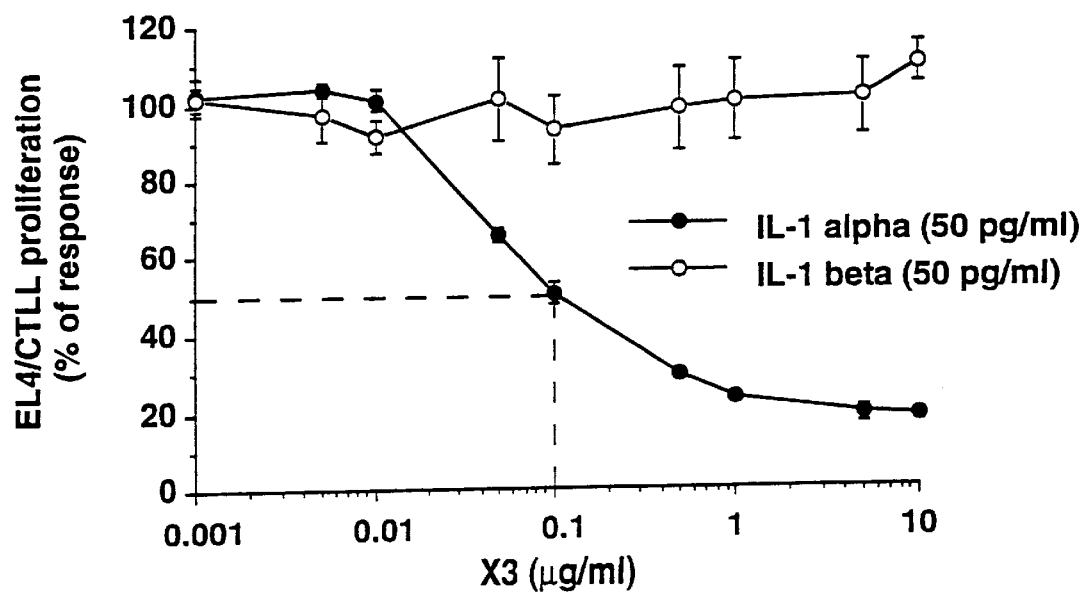
FIG. 4B is a graphical representation showing the EL4/CTLL proliferation (% of response) in the presence of human IL-1β or human IL-1α versus the concentration of HuMAb X3 (μg/ml) in the assay "Inhibition of Human IL-1α-induced IL-2 Secretion by EL4 Cells" described below.

Aliquots of 50 μl of these supernatants were distributed in flat-bottomed microtiter plates and incubated with 50 μl/well of a suspension of IL-2-dependent CTLL cells ($5\times10^4$ cells/ml) which had been washed twice prior to the assay to remove contamination of IL-2 added to maintain their continuous growth. After 36 hours' incubation (37° C., 5% $CO_2$), cells were pulsed for 4 hours with 0.5 μCi/well $^3$H-Thymidine (specific activity: 25 Ci/mmol, CEA, Saclay, France). $^3$H-Thymidine uptake was then measured by standard techniques after harvesting cells on glass fiber filters with a BETAPLATE™ 96-well harvester (Pharmacia) and counting in a BETAPLATE™ liquid scintillation counter (Wallac). Results were expressed in cpm±standard deviation of culture triplicates and are shown in FIG. 4.

The human monoclonal antibody X3 specifically inhibits human IL-1α-induced IL-2 production by EL4 cells, but not the IL-2 secretion induced by human IL-1β. The concentration of antibody X3 required to block 50% of IL-2 secretion induced by 50 pg/ml (2.8 pM) human IL-1α ($IC_{50}$) was found to be 0.1 μg/ml (700 pM).

Inhibition of Human IL-1α-induced IL-6 Production by Human Synoviocytes

Human synoviocytes were isolated from rheumatoid synovial biopsies obtained from rheumatoid arthritis patients.

Different concentrations of the human monoclonal antibody X3 were incubated for 30 minutes at 37° C. with various concentrations of recombinant human IL-1α or human IL-1β in a final volume of 100 μl/well in flat-bottomed microtiter plates (Falcon). Each experimental point was done in triplicate and reagent dilutions were performed in culture medium composed of α-MEM (Gibco) supplemented with 2 mM L-glutamine, 10% heat-inactivated FCS, 50 μg/ml gentamycin and 20 mM Hepes. Then, 100 μl/well of a suspension of human synoviocytes ($5\times10^4$ cells/ml in culture medium described above) were added. After 7 days of incubation (37° C., 5% $CO_2$) supernatants were harvested and tested for their human IL-6 concentrations using a specific ELISA.

Figure 5A:
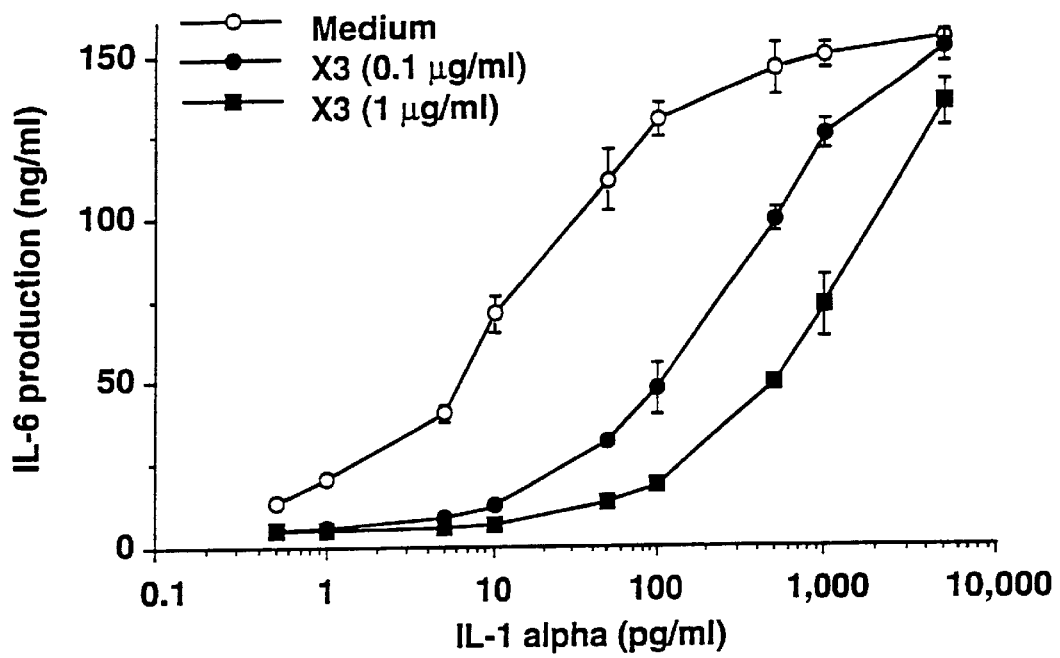
FIG. 5A is a graphical representation showing the IL-6 production (ng/ml) in the presence of either 0.1 μg/ml or μg/ml of HuMAb X3 versus the concentration of IL-1α (pg/ml) in the assay "Inhibition of Human IL-1α-induced IL-6 Production by Human Synoviocytes" described below.
Figure 5B:
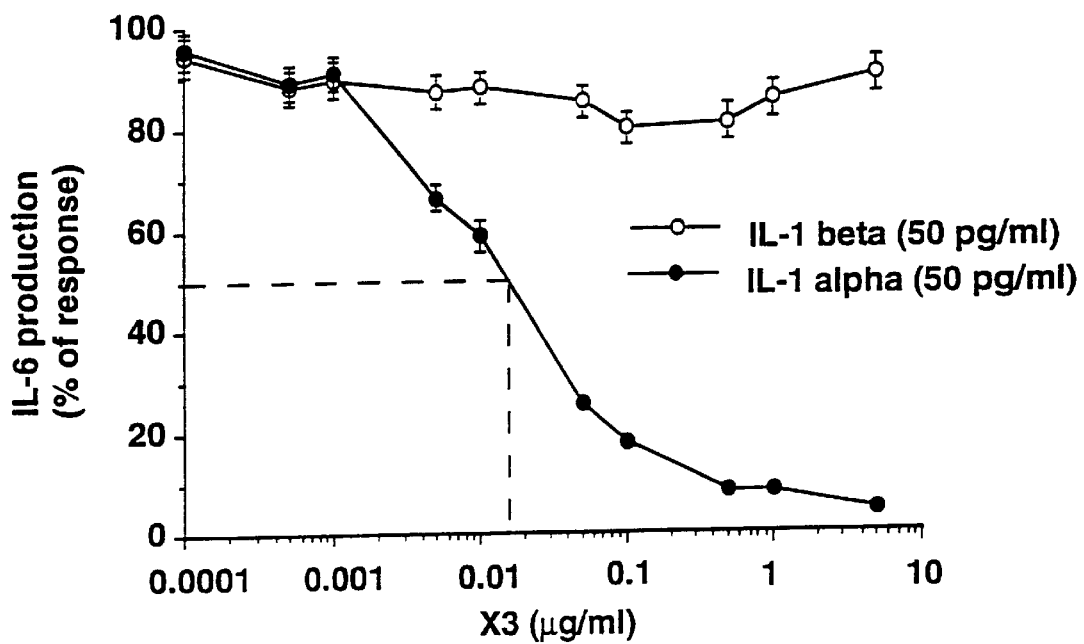
FIG. 5B is a graphical representation showing the IL-6 production (% of response) in the presence of either human IL-1β or IL-1α versus the concentration of HuMAb X3 (μg/ml) in the assay "Inhibition of Human IL-1α-induced IL-6 Production by Human Synoviocytes" described below.

Results shown in FIG. 5 indicate that the human monoclonal antibody X3 specifically inhibits human IL-1α-induced IL-6 production by human synoviocytes, but not the IL-6 secretion induced by human IL-1β. With a constant concentration of 50 pg/ml (2.8 pM) human IL-1α, the $IC_{50}$ was found to be 0.02 μg/ml (150 pM) of human monoclonal antibody X3.

Inhibition of Native Human IL-1α Biological Activity

All the experiments described above were performed using a recombinant form of human IL-1α. In order to demonstrate that the human antibody X3 also neutralizes the biological activity of native human IL-1α, we tested the ability of the antibody X3 to inhibit IL-1-related activities contained in conditioned media or lysates of human mononuclear cells stimulated with lipopolysaccharide (LPS).

To produce native IL-1, PBMNC were isolated from healthy donors by centrifugation on standard Ficoll™ density gradient. PBMNC were washed and $10^7$ cells were then incubated at 37° C. under 5% $CO_2$ in one well of a 6-well tissue-culture plate (Falcon) in 2.5 ml complete culture medium which consisted of RPMI 1640 supplemented with 2 mM L-glutamine, 10% FCS and 50 μg/ml gentamycin. After 1 hour's incubation, non-adherent cells were removed and the adherent cells were washed three times with culture medium maintained at 37° C. Then adherent cells were re-cultured for 24 hours in 2.5 ml complete culture medium containing 1 μg/ml LPS (*E. coli*, serotype 0111:B4) (Sigma Chemical Co.). After this incubation period, supernatant corresponding to the conditioned medium was harvested and centrifuged to remove contaminating cells. Adherent cells were washed three times with cold PBS and removed by treatment at 4° C. with EDTA 0.02% (Sigma) and gentle scrapping with a rubber policeman. Cells were then washed twice, centrifuged, resuspended in 500 μl culture medium and lysed by successive freezings in liquid nitrogen. The cell lysate was then centrifuged (10,000×g, 15 min, 4° C.) and the upper phase was collected and adjusted to 1 ml with complete culture medium.

The ability of the human monoclonal antibody X3 to block the native human IL-1 activity contained in conditioned medium or lysate from LPS-stimulated adherent human mononuclear cells was investigated using the EL4/CTLL assay, because such conditioned medium and lysate may contain significant amounts of LPS and IL-6 which may interact in the synoviocyte assay, but not in the EL4/CTLL assay.

Serial dilutions of conditioned medium or lysate from LPS-stimulated adherent cells were preincubated for 30 minutes without or with 1 µg/ml purified antibody X3, 1 µg/ml non-related IgG$_4$/κ human monoclonal antibody (as negative control) or 1 µg/ml rabbit neutralizing antibodies against human IL-1α (Genzyme) (as positive control). Each condition was done in triplicate, in 96-well flat-bottomed culture plates under a final volume of 100 µl/well. Then 100 µl/well of EL4 cells (5×10$^5$ cells/ml) were added and incubated 24 hours at 37° C. under 5% $CO_2$ in humidified incubator. Culture supernatants were then collected and their IL-2 concentrations were determined using the CTLL assay.

Results presented in Table 4 below show that the human antibody X3 inhibited the IL-1 activity contained in lysate but not in conditioned medium obtained from LPS-stimulated human mononuclear cells. The neutralizing rabbit anti-human IL-1α antiserum shared the same activities as antibody X3, while the unrelated human antibody did not inhibit the IL-1 activity neither in conditioned medium, nor in cell lysate. These results indicate that the antibody X3 recognizes and neutralizes human native IL-1α (which is mostly present in the cytosol and associated with the membrane of LPS-stimulated monocytes), but not native IL-1β (which is principally secreted after LPS-stimulation).

TABLE 4

Inhibition of native human IL-1 by antibody X3

| LPS-stimulated adherent MNC Preparation | Dilution | EL4/CTLL proliferation [$^3$H]-Thymidine uptake (cpm × 10$^{-3}$) | | | |
|---|---|---|---|---|---|
| | | Medium | IgG$_4$/κ | X3 | Rabbit anti-IL-1α |
| Lysate | 1/40 | 84.4 | 115.4 | 18.2 | 22.2 |
| | 1/400 | 26.8 | 35.7 | 2.9 | 4.2 |
| Supernatant | 1/400 | 85.8 | 98.0 | 82.9 | 89.4 |
| | 1/4000 | 5.5 | 4.9 | 5.1 | 4.2 |

The reactivity of HuMAb X3 with Cynomolgus IL-1 was also tested. Monkey blood mononuclear cells were isolated, stimulated with LPS and lysed after 24 hours' incubation. Increasing concentrations of lysate induced EL-4 cells to secrete IL-2, and this activity was inhibited by the polyclonal rabbit anti-human IL-1α. HuMAb X3 was also able to block the monkey IL-1α, but its activity appeared to be lower than that observed with human IL-1α.

Inhibition of Membrane-Associated Human IL-1α Activity

The reactivity of HuMAb X3 with membrane-associated IL-1α was studied by using highly purified human monocytes metabolically inactivated after paraformaldehyde (PFA) fixation. Monocytes were isolated from peripheral blood by elutrial centrifugation essentially as described by De Mulder et al., *J. Immunol. Methods,* 47:31–38 (1981). Purity of the different fractions obtained was assessed by flow cytometry analysis, and preparations containing more than 90% CD14 positive cells were selected. Monocytes were then cultured with or without LPS (1 µg/ml) in Teflon cell culture bags for 24 hours at 37° C., 5% $CO_2$. Then cells were washed twice in PBS and resuspended in PBS containing 1% PFA (Sigma) for 10 minutes at 20° C. Cells were then washed three times with glycine buffer (150 mM glycine, 75 mM NaCl, pH 7.4) and three times with RPMI 1640 complete culture medium. Serial dilutions of PFA-fixed monocytes were then incubated 30 minutes at 37° C. in a final volume of 100µl/well with or without either 1 or 10 µg/ml monoclonal antibody X3, or 10 µg/ml rabbit anti-IL-1α or anti-IL-1β antiserum. Cultures were performed in flat-bottomed 96-well culture plates. Then 100 µl of EL4 suspension (5×10$^5$ cells/ml) were added to each well. After 48 hour's incubation, IL-2 secretion was measured with the CTLL-2 assay as previously described. Results are presented in FIG. 6.

The human monoclonal antibody X3 was found to inhibit IL-2 secretion by EL4 cells induced by PFA-fixed monocytes, whether or not these were stimulated with LPS. A similar inhibition was obtained with the rabbit anti-IL-1α antibody but not with the rabbit anti-IL-1β antiserum. These results indicate that the HuMAb X3 recognizes and neutralizes human membrane IL-1α.

Inhibition of IL-6 Production in Cocultures of Synoviocytes and Monocytes

To test the effect of HuMAb X3 on the production of IL-6 by the coculture of synoviocytes and monocytes, elutriated blood monocytes were cultured for 24 hours with or without LPS (1 µg/ml) and then fixed or not with PFA as described above. Serial dilutions of monocyte preparations were then incubated for 30 minutes at 37° C. with or without 1 µg/ml of HuMAb X3, 1 µg/ml non-related human IgG$_{4κ}$ antibody or 100 ng/ml of IL-1Ra. Cultures were performed in triplicate in flat-bottomed 96-well culture plates. Then 100 µl of synoviocyte suspension (5×10$^4$ cells/ml) were added to each well. After 48 hours of incubation, IL-6 secretion was measured in supernatants with a specific ELISA. Controls performed without synoviocytes showed that, in contrast to unfixed monocytes, PFA-fixed monocytes were unable to secrete IL-6. The results are shown in FIG. 7.

The rheumatoid synovial tissue is composed of about 20% monocyte/macrophage/dendritic cells, 20% fibroblast-like cells (synoviocytes) and 30–50% T cells. This inflammatory tissue produces in vivo and ex vivo high levels of proinflammatory cytokines, including IL-6, TNF-α and IL-1β; see Miossec et al., *Arthritis Rheum.,* 35:874–883 (1992). A coculture of freshly isolated monocytes with synoviocytes from long term cultures results in the production of large amounts of IL-6 but not of IL-10, IL-1β or TNF-α. Furthermore, a coculture of synoviocytes with PFA-fixed monocytes (unable to secrete IL-6) also produced large amounts of IL-6. This indicates that IL-6 is most likely produced by synoviocytes following contact with monocytes.

As shown in FIG. 7, HuMAb X3 was found to strongly inhibit the production of IL-6 by coculture of synoviocytes with non-activated monocytes or LPS-stimulated monocytes (without or with PFA fixation). This finding is in accordance with the inhibitory effect of IL-1Ra. Thus, HuMAb X3 is able to interrupt an interaction between monocytes and synoviocytes, and that interaction may represent a critical step in the development of rheumatoid inflammation.

Sequencing of the Variable Region Genes of the Anti-IL-1α HuMAb X3

RNA from the B cell clone X3 has been isolated according to the single-step method described by Chomczynski et al., *Anal. Biochem.,* 162:156–159 (1987). Briefly, about 10$^7$ cells from this clone were lysed in guanidinium thiocyanate denaturing solution. After acidification of the mixture with 2M sodium acetate, pH4, RNA was extracted with phenol and chloroform/isopentyl alcohol (24:1). RNA was then precipitated with isopropanol, the RNA pellet was redissolved in denaturing solution, reprecipitated with isopropanol, and washed with 75% ethanol.

cDNA was obtained by reverse transcription, using the Superscript Reverse Transcriptase Kit (cat. 20898 BRL, Gaithersburg, Md., USA), with oligo $dT_{12-18}$ primers (Cat. 27.7858-01, Pharmacia, Uppsala, Sweden). The cDNA was then used as template in the PCR. PCR amplifications were performed with Taq polymerase (Perkin Elmer, Norwalk, Conn.) using the reaction buffer provided by the manufacturers: Taq buffer: 1.5 mM $MgCl_2$, 50 mM KCl, 10 mM Tris-HCl, pH 8.3 and 0.001% (w/v) gelatin. All PCR mixtures contained 200 ng of each primer, and 2.5 of Taq Polymerase. Amplifications were performed in a Trio-Thermoblock Thermal cycler (Biometra, GmbH) and consisted of 35 cycles of 1 minute denaturation at 94° C., 2 min of primer annealing at 60° C., and 3 minutes extension at 72° C. After the last cycle, the reaction mixtures were incubated for 10 minutes at 72° C. to insure complete extension of all products. The primers were designed to include restriction sites, to allow for the directional cloning of the PCR products. For the heavy chain, primers (listed in SEQ ID NOS. 3, 4, 5, 6, 7 and 8) specific for the leader sequence of the six different human $V_H$ families were used individually in conjunction with a primer (listed in SEQ ID NO. 9) located at the 3'-end of the gamma-constant region corresponding to the sub-class previously determined by isotyping the HuMAb by ELISA (IgG4). The light chain was amplified with individual combinations of primers corresponding to the 3'-end of the kappa or lambda chain (listed in SEQ ID NOS. 10 and 11, respectively) in conjunction with a series of primers (listed in SEQ ID NOS. 12, 13, 14, 15, 16 and 17) annealing to the leader sequence of the different V kappa gene families or with a series of primers (listed in SEQ ID NOS. 18, 19, 20, 21 and 22) annealing to the leader sequence of the different V lambda gene families. Thus, full-length heavy and light chains starting at the initiation codon in the leader sequence and ending at the stop codon have been generated. Two independent PCRs were performed for both the heavy and the light chains.

Those PCR products were loaded on agarose gels, and purified with GELase (Epicentre, cat. G21223, WI) according to the manufacturer's instructions. Purified PCR products from heavy and light chains were used as template for sequencing reaction with leader PCR primers and with primer hybridizing at the 5'-end of the gamma and of the kappa or lambda constant-region gene respectively. The sequencing reaction was performed on a 373 DNA Sequencer with TaqDyeDeoxy Terminator Cycle Sequencing Kit (both from Applied Biosystems Inc. Foster City, Calif.). Direct sequencing of both strands of the products of two independent PCRs were therefore obtained and compared. No difference was found between the sequences of the two PCRs from the same cells. The sequence of the $V_H$ gene is listed in SEQ ID NO. 1 and the sequence of the $V_L$ gene is listed in SEQ ID NO. 2 below. Framework (FR) and complementarity-determining regions (CDR) are as identified below, in agreement with the system of Kabat et al. (Kabat, E. A., T. T. Wu, H. M. Perry, K. S. Gottesman and C. Foeller (1987), *Sequences of Proteins of Immunological Interest*, United States Department of Health and Human Services, Bethesda, Md., p. 1).

| amino acid residue nos. | region |
|---|---|
| $V_H$ Segment - SEQ ID NO. 1 | |
| −1 to −18 | Signal peptide |
| +1 to +30 | FR 1 |
| +31 to +35 | CDR 1 |
| +36 to +49 | FR 2 |
| +50 to +66 | CDR 2 |
| +67 to 98 | FR 3 |
| +99 to +110 | CDR 3 |
| +111 to +122 | JH 1 |
| $V_L$ Segment - SEQ ID NO. 2 | |
| −1 to −22 | Signal peptide |
| +1 to +23 | FR 1 |
| +24 to +34 | CDR 1 |
| +35 to +49 | FR 2 |
| +50 to +56 | CDR 2 |
| +57 to 88 | FR 3 |
| +89 to +95 | CDR 3 |
| +96 to +108 | JK 4 |

Sequences were compared with the Gene Bank release 77 using the DNAstar (WI, USA) software:

For the heavy-chain sequence (SEQ ID NO. 1), the most homologous sequence encoded was found to be HUMIGHYMG, a human $V_H3$ germine gene [Olee et al., *J. Clin. Invest.*, 88:193–203 (1991)]. However, the level of homology was only 91.6% (25 nucleotide mismatches out of 300 nucleotides), suggesting that the germline counterpart of HuMAb X3 heavy chain is probably different from HUMIGHYAAG. It is therefore currently impossible to assign mutation to any of the mismatches observed in the $V_H$ segment. D segments are not unambiguously identifiable. There is one replacement mutation in the JH1 segment (120 Val/Phe).

For the light-chain sequence (SEQ ID NO. 2), the most homologous sequence encoded was found to be HUMIGKVJ2, a human Vkl germline gene [Pech et al., *J. Mol. Biol.*, 176:189–204 (1984)]. The level of homology reaches 94.7% (14 nucleotide mismatches out of 264 nucleotides) strongly suggesting that the germline counterpart of HuMAb X3 light chain is indeed HUMIGKVJ2. Analysis of somatic mutations in the $V_L$ segment showed the following: the ratio of replacement mutations (R) vs. silent mutations (S) is R/S=5/1 in the CDRs, while R/S is 1/7 in the framework segments (FRs). D segments are not unambiguously identifiable. There are three replacement mutations and one silent mutation in the JK4. In conclusion, the kappa light chain of HuMAb X3 is heavily mutated, and the ratio of R/S mutations in the CDRs vs FRs suggests strong selection by the antigen.

Expression of Recombinant Anti-IL-1α HuMAb In Baculovirus

RNA from the B cell clone X3A-16G5 was isolated by the guanidinium thiocyanate single-step method described by Chomczynski et al., supra. cDNA was obtained by reverse transcription of the RNA using a Superscript Reverse Transcriptase Kit with oligo $dT_{12-18}$ primers (Cat. 27.7858-01, Pharmacia, Uppsala, Sweden). The cDNA was then used as a template in the PCR performed with Taq polymerase. The primers were designed to include EcoR1 and Not1 restriction sites, to allow for the directional cloning of the PCR products into the baculovirus vector pVL-1393. For the heavy chain, primer (listed in SEQ ID NO. 5) specific for the $V_H3$ leader sequence of the human $V_H$ family was used in conjunction with a primer (listed in SEQ ID NO. 9) located at the 3'-end of the gamma constant region corresponding to the sub-class previously determined by isotyping the HuMAb by ELISA (IgG$_4$). The light chain was amplified with a primer (listed in SEQ ID NO. 10) corresponding to the 3'-end of the kappa chain in conjunction with a primer (listed in SEQ ID NO. 12) annealing to the leader sequence of the V kappa 1 gene family. Thus, full-length heavy and light chains cDNAs were generated. Two independent PCRs were performed for both the heavy and the light chains.

After appropriate restriction cleavage of these PCR products, both full-length heavy and light chains were cloned in baculovirus vector restricted with the same enzymes. Heavy and light chains were cloned individually in distinct pVL1393 baculovirus vectors (Invitrogen Co, San Diego, Calif.). The recombinant vectors were transfected in competent DH5α$E$. $coli$ bacteria (Gibco BRL, Gaithersburg, Md.), and 10 single colonies were selected. 100 ml culture of each bacterial clone were obtained, and vector DNA was purified with Qiagen plasmid-Kit (Diagen, GmbH). Both strands of the complete insert from double-stranded DNA vector were sequenced with (1) two primers flanking the insert—the first (listed in SEQ ID NO. 23) annealing 5' in the promoter region of the polyhedrin gene and the second (listed in SEQ ID NO. 24) annealing 3' in the polyhedrin gene itself; and (2) a series of forward primers and backward primers distributed about 400 bp apart along the heavy- and the light-chain sequences; i.e., the forward primers for the heavy chain are listed in SEQ ID NOS. 25 and 26, the backward primers for the heavy chain are listed in SEQ ID NOS. 27, 28 and 29, and the backward primer for the light chain is listed in SEQ ID NO. 30. Double-stranded DNA sequencing was done on a 373 DNA Sequencer with TaqDyeDeoxy Terminator Cycle Sequencing Kit (both from Applied Biosystems Inc., Foster City, Calif.). A recombinant baculovirus vector clone was selected for both the heavy and the light chains, which showed perfect match with the variable-region sequences obtained from the PCR products, and with the published sequences of the constant regions of the heavy gamma 4 and kappa light chains respectively. Recombinant baculovirus vectors were cotransfected with wild type baculovirus DNA in Sf9 insect cells, using the transfection module (Invitrogen Co, San Diego, Calif.). Recombinant baculoviruses recovered from the cell culture supernatant of these transfected cells were then cloned in Sf9 cells by limiting dilution and screened by hybridization with the labeled inserts. After two runs of cloning, followed by production, recombinant baculoviruses containing the heavy- or the light-chain cDNAs were titrated, and used to infect insect cells at a Multiplicity of Infection (MOI) of 5. After 5 days of culture, production of human heavy or light chain was confirmed by ELISA and/or by in vivo labeling. One baculovirus clone expressing the heavy chain and one expressing the light chain were used to co-infect Sf9 cells, each at a MOI of 5. After 5 days of infection, the presence in the supernatant of an antibody binding specifically to human IL-1α was confirmed by immunoprecipitation.

Figure 8A:
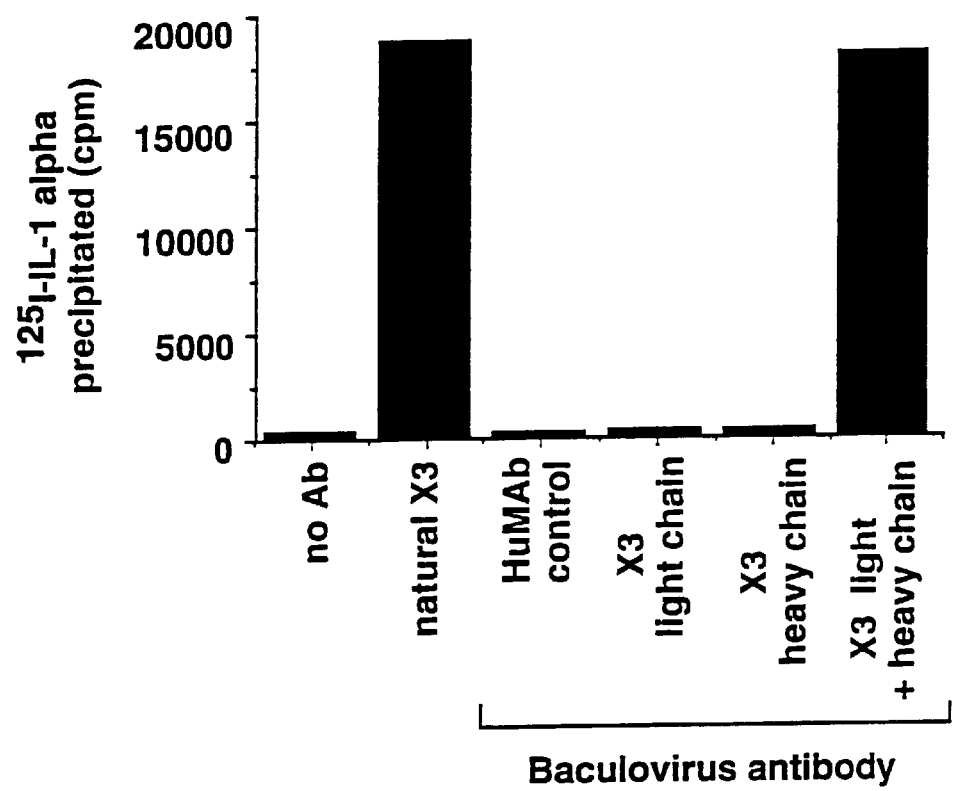
FIG. 8A is a graphical representation showing the amount of $^{125}$I-IL-1α (cpm) precipitated in the assay "Standard Immunoprecipitation Protocol with Protein G" described below with various antibody materials, including the natural HuMAb X3 and the recombinant light and heavy chains from the HuMAb X3.

Supernatants of insect cells infected with (1) recombinant baculovirus containing cDNA of the light chain of X3, (2) with baculovirus containing cDNA of X3 heavy chain, (3) with baculoviruses containing cDNAs of both the X3 heavy and the X3 light chains and (4) with baculoviruses containing cDNAs of both heavy and light chains of a non-related human IgG antibody, were assayed in the Standard Immunoprecipitation Protocol with Protein G described above. The results are shown in FIG. 8A. The results demonstrate that supernatants containing the X3 heavy and light chains precipitated $^{125}$I-IL-1α, while supernatants containing X3 light chain alone, X3 heavy chain alone, or the heavy and light chains of the non-related human IgG did not immunoprecipitate $^{125}$I-IL-1α.

Figure 8B:
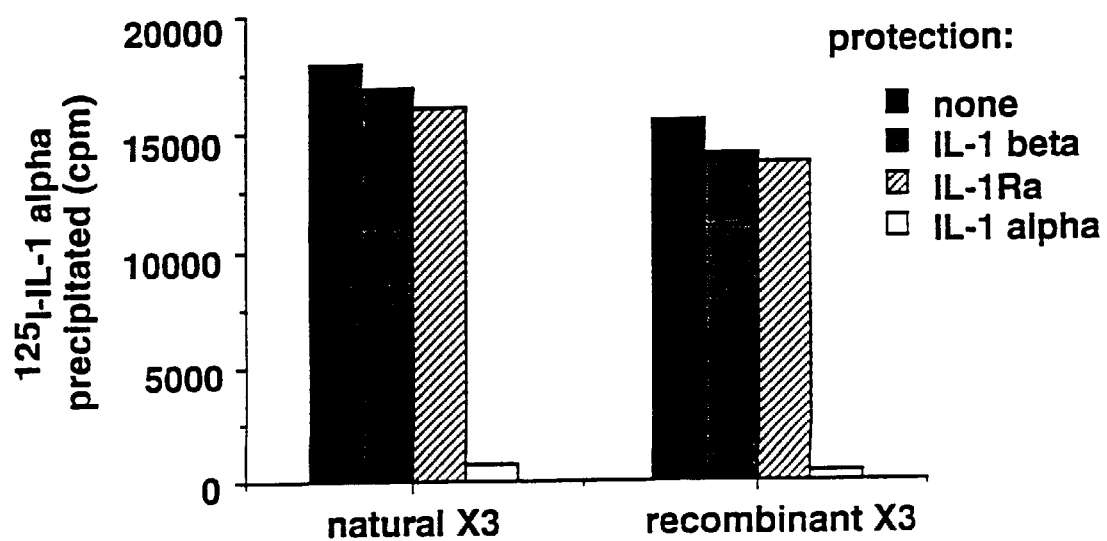
FIG. 8B is a graphical representation showing the amount of $^{125}$I-IL-1α (cpm) precipitated in the assay "Cross-Reactivity of the Human Monoclonal Antibody X3" described below using excess human IL-1β, human IL-1Ra and human IL-1α to protect against immunoprecipitation by natural HuMAb X3 or recombinant HuMAb X3.

Furthermore, the natural HuMAb X3 and the recombinant form of X3 were employed in the assay "Cross-Reactivity of the Human Monoclonal Antibody X3" described above. The results are shown in FIG. 8B, which demonstrate that, as with the natural HuMAb X3, the recombinant form of X3 specifically recognized human IL-1α, since the $^{125}$I-IL-1α immunoprecipitation was not protected by preincubation of X3 with an excess of unlabeled human IL-1β and IL-1Ra.

Figure 9B:
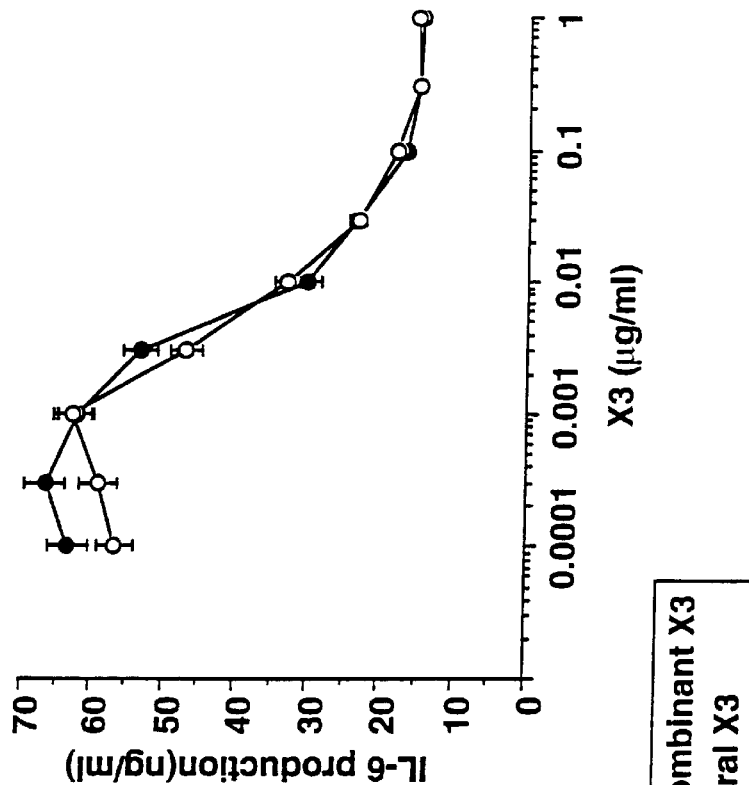
FIG. 9B is a graphical representation showing IL-6 production (ng/ml) versus the concentration of purified natural HuMAb X3 or the concentration of purified recombinant HuMAb X3 (μg/ml) in the assay "Inhibition of Human IL-1α-induced IL-6 production by Human Synoviocytes" described below.
Figure 9A:
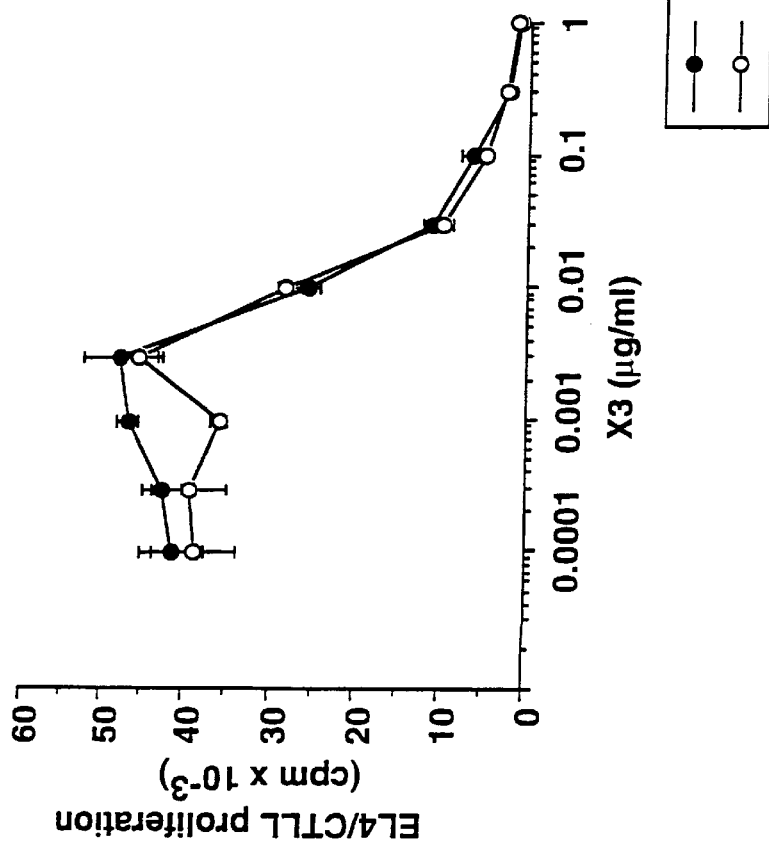
FIG. 9A is a graphical representation showing EL4/CTLL proliferation—[$^3$H]TdR uptake(cpm) versus the concentration of purified natural HuMAb X3 (μg/ml) in the assay "Inhibition of Human IL-1α-induced IL-2 Secretion by EL4 cells" described below.

This recombinant form of X3 was purified from Sf9 cell conditioned medium on a protein G column as previously described for the purification of natural HuMAb X3. The purified recombinant X3 was assayed in the assay "Affinity for Human IL-1α" described above. The obtained equilibrium affinity constant (K$_a$) value was $1.4 \times 10^{10} M^{-1}$. Finally, the purified recombinant X3 was assayed in the assays "Inhibition of Human IL-1α-induced IL-2 Secretion by EL4 cells" and "Inhibition of Human IL-1α-induced IL-6 production by Human Synoviocytes" described above. Results shown in FIG. 9A and FIG. 9B indicate that the recombinant HuMAb X3 inhibited human IL-1α biological activity with the same efficiency as the natural HuMAb X3.

Repertoire Cloning

As demonstrated above, by dilution cloning of an immortalized and/or activated B cell population in accordance with the present invention, a series of amplified B cell subpopulations can be provided for screening for antibodies that bind to the desired antigen, e.g., by the standard and derived immunoprecipitation protocols described above. Thus, by using the immortalization, amplification and screening techniques of the present invention, it is possible to produce and identify an immortalized and/or secreting B cell subpopulation that consists of from about 5 to about 50 different, amplified B cell clones, at least one of which expresses a HuMAb against the desired antigen, e.g. a human cytokine such as IL-1β, TNF-α, IL-6, IL-10 etc.

For example, as discussed above, we produced amplified, immortalized and/or secreting B cell subpopulations from 15 patients expressing HuMAbs against human IL-1α. Each of these subpopulations contained from about 5 to about 50 different amplified B cell clones in a total number of about $5 \times 10^5$ to about $50 \times 10^5$ B cells.

Thus, the percentage of B cells producing HuMAbs against the antigen of interest in a B cell subpopulation of the present invention is greatly enhanced in comparison to other techniques which start with naturally occurring B cell populations. This amplified subpopulation can make it possible to uncover HuMAbs to human cytokines even when isolating a single clone, as we accomplished with the X3 clone discussed above, is not possible.

Starting with an amplified, immortalized and/or secreting B cell subpopulation in accordance with the present invention, including, for example, 40 different B cell clones, the number of possible V$_H$/V$_L$ combinations from a cDNA library encoding the V$_H$ segments and V$_L$ segments from these B cells is 1600 (40×40). This very low number makes it far easier to isolate the specific combination of V$_H$ and V$_L$ segments responsible for the one (or more) amplified HuMAb clone in the subpopulation which binds to the desired antigen. Thus, by applying standard techniques such as repertoire cloning and phage display to the amplified, immortalized and/or secreting B cell subpopulation of the invention, a series of HuMAbs against the desired antigen can be identified and isolated by recombinant techniques.

For example, a cDNA library encoding the mRNA repertoire of $V_H$ and/or $V_L$ segments of all the HuMAbs expressed in such a subpopulation (e.g., a subpopulation screened as containing a clone expressing a HuMAb to IL-10) can be prepared by PCR amplification of the mRNA from the subpopulation using appropriate primers. These repertoire cloning techniques are now standard in the art; see, for example, Marks et al., *J. Mol. Biol.*, 222:581–597 (1991); Huse et al., *Science*, 246:1275–1281 (1989); WO 90/14430; WO 92/15678; WO 91/16427; and WO 92/01047. The DNAs encoding the $V_H$ and $V_L$ segments may be assembled into appropriate vectors for direct cloning and expression in a host, e.g., by the methods described in Hoogenboom et al., *Nucleic Acids Research*, 19:4133–4137 (1991). The expressed $V_H$ and $V_L$ segments or Fab (e.g., for an anti-IL-10 HuMAb) may then be screened for binding to the desired antigen by the standard and derived immunoprecipitation protocols described above using labeled antigen, e.g. $^{125}$I-IL-10. The DNA encoding the $V_H$ or $V_L$ segments from the identified clones can then be sequenced and operatively linked to DNA segments encoding the constant regions for the desired HuMAb isotype heavy or light chains, e.g., heavy chains or κ or λ light chains of $IgG_1$, $IgG_2$, $IgG_3$, $IgG_4$, IgA, etc., to create a complete HuMAb or a fragment thereof (e.g., Fab, F(ab')$_2$, Fv etc.) against the desired antigen, e.g., human IL-10.

Alternatively, the cDNA repertoire encoding the $V_H$ and/or $V_L$ segments can be included in a vector appropriate to display the $V_H$ and/or $V_L$ segments on the surface of a suitable host. See, for example, Marks et al., *J. Mol. Biol.*, 222:581–597 (1991) and Hoogenboom et al., supra, which disclose methodologies for displaying Fv, scFv or Fab fragments of such a cDNA library on the surface of bacteriophage. The host cells (e.g., phage) displaying the scFv on their surface that bind to the desired antigen can then be identified by ELISA or any other suitable assay. The DNA encoding the $V_H$ and/or $V_L$ segments from binding host cells can be separated and reassembled into appropriate vectors for direct cloning and expression in a host, e.g., by the method described in the Marks et al. article. The DNA sequences can then be assembled into a full-length HuMAb) or fragment thereof by the methodologies described above.

An amplified B-cell subpopulation of the present invention as described above may be employed with single cell and multiple cell PCR techniques to yield the DNA sequences encoding the variable regions of the HuMAbs produced by these cells. For example, a CD40-crosslinked B cell population of the invention (which may also be EBV-transformed) may be diluted to provide either a small number of B cells (e.g., 10 B cells per well) or (on average) a single B cell or less per well. The methodologies disclosed, for example, in Larrick et al., *Biotechnology*, 7:934 (1989), Embleton et al., *Nucleic Acids Research*, 10:3831–3837 (1992), Liu et al., *Proc. Natl. Acad. Sci.*, 89: 7610–7614 (1992), and Lew et al. *Immunology*, 75:3–9 (1992), may be employed to obtain accurate and complete heavy- and light-chain variable region genes ($V_H$ and $V_L$ genes) from these cells. These DNA sequences may be included in an appropriate recombinant system to express, for example, an Fv or scFv, and the fact that they represent a HuMAb to the desired antigen may then be confirmed by the immunoprecipitation assays described above for binding to the desired antigen. Previous isotyping of the active HuMAbs in the B-cell starting population or subpopulation may then be used to construct the full-length HuMAb.

The activity of the HuMAb may then be confirmed by conventional in vitro and in vivo biological assays. For example, for TNF-α, IL-1β and IL-6, the assays and models reviewed in Dinarello, *Eur. Cytokine Netw.*, 3:7–17 (1992) may be employed. For human IL-10 the cytokine synthesis inhibitory factor (CSIF) assay described in Florentino et al., *J. Exp. Med.*, 170:2081–2095 (1989) or the property of IL-10 to induce proliferation and Ig secretion by human B cellar as described in Rousset et al., *Proc. Natl. Acad. Sci. USA*, 89:1890–1893 (1992) may be employed.

It is most likely that the pairs of heavy and light chains identified under the above conditions will be those of the identified antibody, since the screening procedures described above are selective for high affinity antibody which can only be obtained with a given combination of heavy and light chain. Furthermore, the identification of the heavy- and light-chain isotypes in the supernatants of the oligoclonal cell lines will also be of great help to determine whether the selected pair does indeed correspond to the initially identified clone.

While the present invention has been described in conjunction with the specific embodiments set forth above, many alternatives, modifications and variations thereof will be apparent to those of ordinary skill in the art. All such alternatives, modifications and variations fall within the spirit and scope of the present invention.

We claim:

1. A human monoclonal antibody against a human IL-1α or a human IL-1α binding fragment of said antibody characterized in that it comprises a complementary determining region of an amino acid sequence defined by amino acids 1–122 of an amino acid sequence encoded by the nucleic acid sequence shown in SEQ ID NO:1 or by a complementary determining region somatic variant thereof and/or of an amino acid sequence defined by amino acids 1–108 of an amino acid sequence encoded by the nucleic acid sequence shown in SEQ ID NO:2; or by a complementary determining region somatic variant thereof.

2. A human monoclonal antibody against a human IL-1α or a human IL-1α binding fragment of said antibody characterized in that it comprises a $V_H$ segment having an amino acid sequence defined by amino acids 1–122 of an amino acid sequence encoded by the nucleic acid sequence shown in SEQ ID NO:1 or by a complementary determining region somatic variant thereof, and/or a $V_L$ segment having an amino acid sequence defined by amino acids 1–108 of an amino acid sequence encoded by the nucleic acid sequence shown in SEQ ID NO:2 or by a complementary determining region somatic variant thereof.

3. The antibody or fragment according to claim 2, characterized in that it comprises a $V_H$ segment having an amino acid sequence defined by amino acids 1–122 of an amino acid sequence encoded by the nucleic acid sequence shown in SEQ ID NO:1 and/or a $V_L$ segment having an amino acid sequence defined by amino acids 1–108 of an amino acid sequence encoded by the nucleic acid sequence shown in SEQ ID NO:2.

4. The antibody according to claim 2, characterized in that it comprises $V_H$ and $V_L$ segments having the amino acid sequences defined by amino acids 1–122 of an amino acid sequence encoded by the nucleic acid sequence shown in SEQ ID NO:1 and amino acids 1–108 of an amino acid sequence encoded by the nucleic acid sequence shown in SEQ ID NO:2, respectively, or which comprises a complementary determining region somatic variant of one or both of said amino acid sequences.

5. The antibody according to claim 2, characterized in that it is the $IgG_4$ isotype.

6. The fragment according to claim 3, characterized in that it comprises a Fv, single-chain Fv, Fab or F(ab')$_2$ fragment.

7. An isolated nucleic acid characterized in that it comprises: a nucleotide sequence defined by base numbers 58423 of SEQ ID NO:1 or by a complementary determining region encoding somatic variant thereof, and/or a nucleotide sequence defined by base numbers 67–390 of SEQ ID NO:2 or by a complementary determining region encoding somatic variant thereof.

8. An isolated nucleic acid according to claim 7, characterized in that it comprises a nucleotide sequence defined by base numbers 58–423 of SEQ ID NO:1 and/or base numbers 67–390 of SEQ ID NO:2.

* * * * *

SEQUENCE LISTING (1) GENERAL INFORMATION:

(iii) NUMBER OF SEQUENCES:   30

(2) INFORMATION FOR SEQ ID NO: 1:

(i) SEQUENCE CHARACTERISTICS:
      (A) LENGTH:   423 base pairs
      (B) TYPE:   nucleic acid
      (C) STRANDEDNESS:   double
      (D) TOPOLOGY:   linear (xi) SEQUENCE DESCRIPTION: SEQ ID NO: 1:

```
ATG GAG TTT GGG CTG AGC TGG GTT TTC CTC GTT GCT CTT TTA AGA GGT      48
Met Glu Phe Gly Leu Ser Trp Val Phe Leu Val Ala Leu Leu Arg Gly
```

```
                -15                 -10                 -5
GTC CAG TGT CAG GTG CAA CTG GTG GAA TCT GGG GGA GGC GTG GTC CAG    96
Val Gln Cys Gln Val Gln Leu Val Glu Ser Gly Gly Gly Val Val Gln
        +1                   5                  10

CCT GGG AGG TCC CTG AGA CTC TCC TGT ACA GCC TCT GGA TTC ACC TTC   144
Pro Gly Arg Ser Leu Arg Leu Ser Cys Thr Ala Ser Gly Phe Thr Phe
        15                  20                  25

AGT ATG TTT GGT GTC CAC TGG GTC CGC CAG GCC CCA GGC AAG GGG CTG   192
Ser Met Phe Gly Val His Trp Val Arg Gln Ala Pro Gly Lys Gly Leu
30                      35                  40                  45

GAG TGG GTG GCA GCT GTG TCA TAT GAT GGA AGC AAT AAG TAC TAT GCA   240
Glu Trp Val Ala Ala Val Ser Tyr Asp Gly Ser Asn Lys Tyr Tyr Ala
                    50                  55                  60

GAG TCC GTG AAG GGC CGA TTC ACC ATC TCC AGA GAC AAT TCC AAG AAC   288
Glu Ser Val Lys Gly Arg Phe Thr Ile Ser Arg Asp Asn Ser Lys Asn
            65                  70                  75

ATC TTA TTT CTA CAA ATG GAC AGC CTG AGA CTT GAG GAC ACG GCT GTC   336
Ile Leu Phe Leu Gln Met Asp Ser Leu Arg Leu Glu Asp Thr Ala Val
        80                  85                  90

TAT TAC TGT GCT AGA GGC CGG CCC AAG GTC GTA ATA CCA GCA CCT TTG   384
Tyr Tyr Cys Ala Arg Gly Arg Pro Lys Val Val Ile Pro Ala Pro Leu
95                  100                 105

GCT CAC TGG GGC CAG GGA ACC CTG GTC ACC TTC TCC TCA                423
Ala His Trp Gly Gln Gly Thr Leu Val Thr Phe Ser Ser
110                 115                 120

(2) INFORMATION FOR SEQ ID NO: 2:

(i) SEQUENCE CHARACTERISTICS:
        (A) LENGTH:     390 base pairs
        (B) TYPE:       nucleic acid
        (C) STRANDEDNESS:  double
        (D) TOPOLOGY:   linear (xi) SEQUENCE DESCRIPTION: SEQ ID NO: 2:

ATG GAC ATG AGG GTC CCC GCT CAG CTC CTG GGG CTC CTG CTG CTC TGG    48
Met Asp Met Arg Val Pro Ala Gln Leu Leu Gly Leu Leu Leu Leu Trp
        -20                 -15                 -10

TTC CCA GGT TCC AGA TGC GAC ATC CAG ATG ACC CAG TCT CCA TCT TCC    96
Phe Pro Gly Ser Arg Cys Asp Ile Gln Met Thr Gln Ser Pro Ser Ser
        -5                  +1                  5                  10

GTG TCT GCA TCT GTA GGA GAC AGA GTC ACC ATC ACT TGT CGG GCG AGT   144
Val Ser Ala Ser Val Gly Asp Arg Val Thr Ile Thr Cys Arg Ala Ser
                    15                  20                  25

CAG GGT ATT AGC AGT TGG TTA GCC TGG TAT CAG CAG AAA CCA GGA AAG   192
Gln Gly Ile Ser Ser Trp Leu Ala Trp Tyr Gln Gln Lys Pro Gly Lys
                30                  35                  40

GCC CCG AAG CTC TTG ATC TAT GAA GCA TCC AAT TTG GAA ACT GGG GTC   240
Ala Pro Lys Leu Leu Ile Tyr Glu Ala Ser Asn Leu Glu Thr Gly Val
        45                  50                  55

CCA TCA AGA TTC AGC GGC AGT GGA TCT GGG TCA GAT TTC ACC CTC ACC   288
Pro Ser Arg Phe Ser Gly Ser Gly Ser Gly Ser Asp Phe Thr Leu Thr
60                  65                  70

ATC AGC AGC CTG CAG CCT GAA GAT TTT GCA ACT TAT TAT TGT CAA CAG   336
Ile Ser Ser Leu Gln Pro Glu Asp Phe Ala Thr Tyr Tyr Cys Gln Gln
75                  80                  85                  90

ACT AGC AGT TTT CTC CTC AGT TTC GGC GGC GGG ACC AAG GTG GAG CAC   384
Thr Ser Ser Phe Leu Leu Ser Phe Gly Gly Gly Thr Lys Val Glu His
                95                  100                 105

AAA CGA                                                            390
Lys Arg
```

(2) INFORMATION FOR SEQ ID NO: 3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 3:

```
CCCGAATTCA TGGACTGGAC CTGGAGG                                    27
```

(2) INFORMATION FOR SEQ ID NO: 4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 4:

```
CCCGAATTCA TGGACATACT TTGTACCAC                                  29
```

(2) INFORMATION FOR SEQ ID NO: 5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 5:

```
CCCGAATTCA TGGAGTTTGG GCTGAGC                                    27
```

(2) INFORMATION FOR SEQ ID NO: 6:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 6:

```
CCCGAATTCA TGAAACACCT GTGGTTCTT                                  29
```

(2) INFORMATION FOR SEQ ID NO: 7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 7:

```
CCCGAATTCA TGGGGTCAAC CGCCATCCT                                  29
```

(2) INFORMATION FOR SEQ ID NO: 8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO: 8:

```
CCCGAATTCA TGTCTGTCTC CTTCCTCAT                                  29
```

(2) INFORMATION FOR SEQ ID NO: 9:

(i) SEQUENCE CHARACTERISTICS:
        (A) LENGTH:  31 base pairs
        (B) TYPE:  nucleic acid
        (C) STRANDEDNESS:  single
        (D) TOPOLOGY:  linear (xi) SEQUENCE DESCRIPTION: SEQ ID NO: 9:

GAGAGAGCGG CCGCACTCAT TTACCCGGAG A                           31

(2) INFORMATION FOR SEQ ID NO: 10:

(i) SEQUENCE CHARACTERISTICS:
        (A) LENGTH:  34 base pairs
        (B) TYPE:  nucleic acid
        (C) STRANDEDNESS:  single
        (D) TOPOLOGY:  linear (xi) SEQUENCE DESCRIPTION: SEQ ID NO: 10:

GAGAGAGCGG CCGCTAACAC TCTCCCCTGT TGAA                        34

(2) INFORMATION FOR SEQ ID NO: 11:

(i) SEQUENCE CHARACTERISTICS:
        (A) LENGTH:  38 base pairs
        (B) TYPE:  nucleic acid
        (C) STRANDEDNESS:  single
        (D) TOPOLOGY:  linear (xi) SEQUENCE DESCRIPTION: SEQ ID NO: 11:

GAGAGAGCGG CCGCCTATGA ACATTCTGTA GGGGCCAC                    38

(2) INFORMATION FOR SEQ ID NO: 12:

(i) SEQUENCE CHARACTERISTICS:
        (A) LENGTH:  36 base pairs
        (B) TYPE:  nucleic acid
        (C) STRANDEDNESS:  single
        (D) TOPOLOGY:  linear (xi) SEQUENCE DESCRIPTION: SEQ ID NO: 12:

CCCGAATTCA TGGACATGAG GGTCCCCGCT CAGCTC                      36

(2) INFORMATION FOR SEQ ID NO: 13:

(i) SEQUENCE CHARACTERISTICS:
        (A) LENGTH:  33 base pairs
        (B) TYPE:  nucleic acid
        (C) STRANDEDNESS:  single
        (D) TOPOLOGY:  linear (xi) SEQUENCE DESCRIPTION: SEQ ID NO: 13:

CCCGAATTCA TGGACACGAG GGCCCCCACT CAG                         33

(2) INFORMATION FOR SEQ ID NO: 14:

(i) SEQUENCE CHARACTERISTICS:
        (A) LENGTH:  29 base pairs
        (B) TYPE:  nucleic acid
        (C) STRANDEDNESS:  single
        (D) TOPOLOGY:  linear (xi) SEQUENCE DESCRIPTION: SEQ ID NO: 14:

CCCGAATTCA TGGTGTTGCA GACCCAGGT                              29

(2) INFORMATION FOR SEQ ID NO: 15:

(i) SEQUENCE CHARACTERISTICS:

(A) LENGTH:  33 base pairs
        (B) TYPE:  nucleic acid
        (C) STRANDEDNESS:  single
        (D) TOPOLOGY:  linear (xi) SEQUENCE DESCRIPTION: SEQ ID NO: 15:

CCCGAATTCA TGAGGCTCCC TGCTCAGCTC CTG                       33

(2) INFORMATION FOR SEQ ID NO: 16:

(i) SEQUENCE CHARACTERISTICS:
        (A) LENGTH:  29 base pairs
        (B) TYPE:  nucleic acid
        (C) STRANDEDNESS:  single
        (D) TOPOLOGY:  linear (xi) SEQUENCE DESCRIPTION: SEQ ID NO: 16:

CCCGAATTCA TGGAAACCCC AGCGCAGCT                            29

(2) INFORMATION FOR SEQ ID NO: 17:

(i) SEQUENCE CHARACTERISTICS:
        (A) LENGTH:  30 base pairs
        (B) TYPE:  nucleic acid
        (C) STRANDEDNESS:  single
        (D) TOPOLOGY:  linear (xi) SEQUENCE DESCRIPTION: SEQ ID NO: 17:

CCCGAATTCA TGGGGTCCCA GGTTCACCTC                           30

(2) INFORMATION FOR SEQ ID NO: 18:

(i) SEQUENCE CHARACTERISTICS:
        (A) LENGTH:  29 base pairs
        (B) TYPE:  nucleic acid
        (C) STRANDEDNESS:  single
        (D) TOPOLOGY:  linear (xi) SEQUENCE DESCRIPTION: SEQ ID NO: 18:

CCCGAATTCA TGACCTGCTC CCCTCTCCT                            29

(2) INFORMATION FOR SEQ ID NO: 19:

(i) SEQUENCE CHARACTERISTICS:
        (A) LENGTH:  33 base pairs
        (B) TYPE:  nucleic acid
        (C) STRANDEDNESS:  single
        (D) TOPOLOGY:  linear (xi) SEQUENCE DESCRIPTION: SEQ ID NO: 19:

CCCGAATTCA TGGCCTGGAC TCCTCTCTTT CTG                       33

(2) INFORMATION FOR SEQ ID NO: 20:

(i) SEQUENCE CHARACTERISTICS:
        (A) LENGTH:  29 base pairs
        (B) TYPE:  nucleic acid
        (C) STRANDEDNESS:  single
        (D) TOPOLOGY:  linear (xi) SEQUENCE DESCRIPTION: SEQ ID NO: 20:

CCCGAATTCA TGGCCTGGGC TCCACTACT                            29

(2) INFORMATION FOR SEQ ID NO: 21:

(i) SEQUENCE CHARACTERISTICS:
        (A) LENGTH:  29 base pairs
        (B) TYPE:  nucleic acid

```
            (C) STRANDEDNESS:  single
            (D) TOPOLOGY:  linear (xi) SEQUENCE DESCRIPTION: SEQ ID NO: 21:

CCCGAATTCA TGGCATGGAT CCCTCTCTT                                      29

(2) INFORMATION FOR SEQ ID NO: 22:

(i) SEQUENCE CHARACTERISTICS:
            (A) LENGTH:  30 base pairs
            (B) TYPE:  nucleic acid
            (C) STRANDEDNESS:  single
            (D) TOPOLOGY:  linear (xi) SEQUENCE DESCRIPTION: SEQ ID NO: 22:

CCCGAATTCA TGGCCTGGGC TCTGCTGCTC                                     30

(2) INFORMATION FOR SEQ ID NO: 23:

(i) SEQUENCE CHARACTERISTICS:
            (A) LENGTH:  25 base pairs
            (B) TYPE:  nucleic acid
            (C) STRANDEDNESS:  single
            (D) TOPOLOGY:  linear (xi) SEQUENCE DESCRIPTION: SEQ ID NO: 23:

ACCTATAAAT ATTCCGGATT ATTCA                                          25

(2) INFORMATION FOR SEQ ID NO: 24:

(i) SEQUENCE CHARACTERISTICS:
            (A) LENGTH:  17 base pairs
            (B) TYPE:  nucleic acid
            (C) STRANDEDNESS:  single
            (D) TOPOLOGY:  linear (xi) SEQUENCE DESCRIPTION: SEQ ID NO: 24:

TCTTGCCGGG TCCCAGG                                                   17

(2) INFORMATION FOR SEQ ID NO: 25:

(i) SEQUENCE CHARACTERISTICS:
            (A) LENGTH:  21 base pairs
            (B) TYPE:  nucleic acid
            (C) STRANDEDNESS:  single
            (D) TOPOLOGY:  linear (xi) SEQUENCE DESCRIPTION: SEQ ID NO: 25:

GGTCTCCAAC AAAGCCCTCC C                                              21

(2) INFORMATION FOR SEQ ID NO: 26:

(i) SEQUENCE CHARACTERISTICS:
            (A) LENGTH:  27 base pairs
            (B) TYPE:  nucleic acid
            (C) STRANDEDNESS:  single
            (D) TOPOLOGY:  linear (xi) SEQUENCE DESCRIPTION: SEQ ID NO: 26:

CACAAGCCCA GCAACACCAA GGTGGAC                                        27

(2) INFORMATION FOR SEQ ID NO: 27:

(i) SEQUENCE CHARACTERISTICS:
            (A) LENGTH:  26 base pairs
            (B) TYPE:  nucleic acid
            (C) STRANDEDNESS:  single
            (D) TOPOLOGY:  linear
```

(xi) SEQUENCE DESCRIPTION: SEQ ID NO: 27:

GGGGGGAAGA GGAAGACTGA CGGTCC                                                26

(2) INFORMATION FOR SEQ ID NO: 28:

(i) SEQUENCE CHARACTERISTICS:
        (A) LENGTH:   28 base pairs
        (B) TYPE:   nucleic acid
        (C) STRANDEDNESS:   single
        (D) TOPOLOGY:   linear (xi) SEQUENCE DESCRIPTION: SEQ ID NO: 28:

GGGTGTACAC CTGTGGTTCT CGGGGCTG                                              28

(2) INFORMATION FOR SEQ ID NO: 29:

(i) SEQUENCE CHARACTERISTICS:
        (A) LENGTH:   21 base pairs
        (B) TYPE:   nucleic acid
        (C) STRANDEDNESS:   single
        (D) TOPOLOGY:   linear (xi) SEQUENCE DESCRIPTION: SEQ ID NO: 29:

GCAGGTGTAG GTCTGGGTGC C                                                     21

(2) INFORMATION FOR SEQ ID NO: 30:

(i) SEQUENCE CHARACTERISTICS:
        (A) LENGTH:   20 base pairs
        (B) TYPE:   nucleic acid
        (C) STRANDEDNESS:   single
        (D) TOPOLOGY:   linear (xi) SEQUENCE DESCRIPTION: SEQ ID NO: 30:

TGGCGGGAAG ATGAAGACAG                                                       20